(12) United States Patent
Pugia et al.

(10) Patent No.: US 10,809,264 B2
(45) Date of Patent: Oct. 20, 2020

(54) RARE MOLECULE DETECTION

(71) Applicant: SIEMENS HEALTHCARE DIAGNOSTICS INC., Tarrytown, NY (US)

(72) Inventors: Michael Pugia, Granger, IN (US); Julia Philip, South Bend, IN (US); Karen Marfurt, Edwardsburg, MI (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 223 days.

(21) Appl. No.: 15/314,860

(22) PCT Filed: May 29, 2015

(86) PCT No.: PCT/US2015/033278
§ 371 (c)(1),
(2) Date: Nov. 29, 2016

(87) PCT Pub. No.: WO2015/184321
PCT Pub. Date: Dec. 3, 2015

(65) Prior Publication Data
US 2017/0102390 A1    Apr. 13, 2017

Related U.S. Application Data

(60) Provisional application No. 62/004,640, filed on May 29, 2014.

(51) Int. Cl.
*G01N 33/58* (2006.01)
*G01N 33/68* (2006.01)
*G01N 1/40* (2006.01)

(52) U.S. Cl.
CPC ....... *G01N 33/585* (2013.01); *G01N 33/6848* (2013.01); *G01N 2001/4088* (2013.01); *G01N 2560/00* (2013.01)

(58) Field of Classification Search
None
See application file for complete search history.

(56) References Cited

U.S. PATENT DOCUMENTS 5,571,513 A * 11/1996 Burstein ............ C07K 16/2866
424/144.1
6,319,690 B1 * 11/2001 Little ...................... C07K 7/06
435/69.6

(Continued)

OTHER PUBLICATIONS

GE Healthcare Life Science 2012, p. 12 and 64 (Year: 2012).*

(Continued)

*Primary Examiner* — Changhwa J Cheu

(57) ABSTRACT

A concentrated sample having enhanced concentration of the one or more different populations of target rare molecules is incubated with, for each different population of target rare molecules, a particulate or non-particulate affinity agent that comprises a specific binding partner that is specific for and binds to a target rare molecule. The affinity agent comprises a mass spectrometry (MS) label precursor or a first alteration agent, which either facilitates the formation of an MS label from the MS label precursor or releases an entity that comprises the MS label precursor from the affinity agent. The MS label corresponds to one of the populations of target rare molecules. A second alteration agent is employed if the first alteration agent does not facilitate the formation of an MS label from the MS label precursor. MS analysis is used to determine each different MS label.

20 Claims, 13 Drawing Sheets

Specification includes a Sequence Listing.

(56) References Cited

U.S. PATENT DOCUMENTS

| | | | |
|---|---|---|---|
| 2009/0137060 A1 | 5/2009 | Lund-Johansen | |
| 2009/0188864 A1* | 7/2009 | Zheng .................. | B01D 61/18 |
| | | | 210/641 |
| 2011/0034488 A1* | 2/2011 | Roa ...................... | A61B 5/153 |
| | | | 514/274 |
| 2013/0023024 A1* | 1/2013 | Ying ...................... | B82Y 5/00 |
| | | | 435/173.9 |
| 2016/0223530 A1* | 8/2016 | Marshall ............ | G01N 33/6848 |

OTHER PUBLICATIONS

International Search Report for Int. App. No. PCT/2015/033278 dated Nov. 10, 2015.
Enzyme Linked Immuno Mass Spectrometric Assay (ELIMSA) Angelique Florentinus-Mefailoski, Frozan Safi, John G. Marshall Department of Chemistry and Biology, Faculty of Science, Ryerson University, Toronto, Canada / Nov. 22, 2013.

* cited by examiner

Method for removing particles and sampling for analysis

RARE MOLECULE DETECTION

BACKGROUND

This application incorporates by reference the sequence listing which is submitted together with this application in computer readable form which has the file name SequenceListing_2014P03334WO_ST25.txt and is 4 KB.

The invention relates to methods and kits for detecting one or more different populations of rare molecules in a blood sample suspected of containing the one or more different populations of rare molecules and non-rare molecules. In some aspects, the invention relates to methods and kits for detecting one or more different populations of rare molecules that are freely circulating in blood. In some aspects, the invention relates to methods and kits for detecting one or more different populations of rare molecules that are associated with rare cells in a blood sample suspected of containing the one or more different populations of rare cells and non-rare cells.

The detection of rare molecules in the range of 1 to 50,000 copies (fentamolar (fM) or less) cannot be achieved by conventional affinity assays, which require a number of molecular copies far above the numbers found for rare molecules. For example, immunoassays cannot typically achieve a detection limit of 1 picomolar (pM). Immunoassays are limited by the affinity binding constant of an antibody, which is typically not higher than $10^{-12}$ (1 pM). Immunoassays require at least 100-fold antibody excess due to the off-rate being $10^{-13}$, and the solubility of the antibody protein limits driving the reaction to completion. As a typical sample volume is rarely greater than 10 μL, a concentration of 1 pM requires 60 million copies of a rare molecule for detection, far greater than the range for a rare molecule. The detection of circulating proteins that are not cell bound is also desirable. This same issue of solubility of the antibody prevents conventional immunoassays from reaching sub-attomolar levels.

The detection of rare molecules can be achieved by conventional nucleic acid assays. However, the target nucleic acids must be subjected to one or more lengthy purification steps and amplifications that can take several days for analysis time. For example, amplification techniques include, but are not limited to, enzymatic amplification such as, for example, polymerase chain reaction (PCR), ligase chain reaction (LCR), nucleic acid sequence based amplification (NASBA), Q-β-replicase amplification, 3SR (specific for RNA and similar to NASBA except that the RNAase-H activity is present in the reverse transcriptase), transcription mediated amplification (TMA) (similar to NASBA in utilizing two enzymes in a self-sustained sequence replication), whole genome amplification (WGA) with or without a secondary amplification such as, e.g., PCR, multiple displacement amplification (MDA) with or without a secondary amplification such as, e.g., PCR, whole transcriptome amplification (WTA) with or without a secondary amplification such as, e.g., PCR or reverse transcriptase PCR, for example.

Cellular analysis is important in medical applications such as, for example, diagnosis of many diseases. The detection of rare molecules that are cell bound or included in the cell is also desire-able. The medical applications of cellular analysis require isolation of certain cells of interest, which typically represent only a small fraction of a sample under analysis. For example, circulating tumor cells ("CTCs") are of particular interest in the diagnosis of metastatic cancers. In conventional methods, CTC are isolated from whole blood by first removing red blood cells (RBCs) by lyses. In a 10 mL blood sample, a few hundred CTCs are to be separated from about 800,000,000 white blood cells ("WBCs"). Therefore, methods with high separation efficiency and cell recovery rates are necessary.

Cell filtration for the separation of rare cells using a porous matrix is a useful method used to sort cells by size and, in most instances, such filtration methods allow for the extraction of cells following separation. Both microfluidic post and microfluidic membrane methods are used in these filtration approaches. However, the existing filtration methods are limited by certain factors, which include, for example, the range of diameters that in vitro cells have rather than a single diameter. This range of diameters is demonstrated, for example, in the case of cancer cell populations and white blood cell populations, which have overlapping diameters. During filtration small cancer cells are lost and larger white blood cells contaminate the separated material. Furthermore, cancer cell populations and white blood cell populations are very heterogeneous and comprise a variety of cell diameter types within these individual populations. For example, the range of diameters for white blood cells is much wider when considering samples including populations of neutrophils, eosinophils, basophils, macrophages, lymphocytes and macrophages. Cancer cells in blood can also range in size.

However, cell filtration techniques can yield only a few rare cells. For example, for a cancer patient a single to several thousand CTCs are typically seen in 10 mL of whole blood. The number of copies of a rare molecule can be significant at only tens of thousands of copies per cell for proteins or a few copies per cell for a gene mutation.

Rare cells can be analyzed down to the single cell level by a conventional scanning microscopy. Antibodies with fluorescent labels can detect as few at 50,000 molecules at 1 attomolar (aM) for some proteins in a single cell. This is due to the extremely small sample detection volume (less than 1 nanoliter (nL)) of a microscopic analysis of a single cell. Additionally, as few as 1,000 molecules (fM) can be detected with antibodies after enzyme amplification (500-fold amplification). Further, molecular analysis (in-situ hybridization) of cells can be done down to a single molecule level due to the higher affinity of nucleic acid probes. However, even with automation of the scanning and analysis, the microscopy method can take 24 hours or more for each sample to be scanned. Additionally, all the rare cells with multiple images must be examined visually by the pathologist to determine the significance of protein amounts measured.

Mass Spectrometry (MS) is an extremely sensitive and specific technique and is very well suited for detecting small molecules (about 300 daltons (Da)) and medium sized molecules (about 3000 Da) at pM concentrations. MS has the ability to simultaneously measure hundreds (multiplexing) of highly abundant components present in complex biological media in a single assay without the need for labeled reagents. The method offers specificity until the biological media causes overlapping masses. Of the MS combined techniques (ionization and separation), triple quad mass spectrometry (MS-MS), liquid chromatography-tandem mass spectrometry (LC-MS/MS) is limited to small mass analytes and liquid chromatography-tandem mass spectrometry (LC-MS/MS) with multiple reaction monitoring (MRM) (LC-MRM-MS) is limited to high abundance proteins. In both cases the use of liquid chromatography makes automation difficult due to run times, cost, complexity and maintainability. Matrix-assisted laser desorption/ ionization using a time-of-flight mass spectrometer (MALDI-TOF) combined technique is well suited for high sensitivity for low abundance molecules needed for rare molecular analysis; however, specificity for the biological media causes overlapping masses.

The current state of the art mass spectroscopy has several issues, which keep MS from being competitive with routine affinity reaction systems. The noted problems are inability to separate markers of interest from sample interference (matrix over lapping peaks), loss of sensitivity due to background in clinical sample (picomolar (pM) reduced to nanomolar (nM)), the inability to work with small nL sample volumes as samples less than 1 microliters (µl) are inefficiently captured for ionization) and inefficiently isolated from interfering peaks in complex samples such as blood. In addition, MS often has an inability to detect certain masses due to competition with other mass of the same mass being ionized. These issues typically cause problems due to false results.

Another problem for mass spectral analysis is that quantitation of results requires mass to ionize readily; this can limit detection to smaller masses of less than 3 kilodaltons (kDa) with atoms that can be charged and made into parent ions. Proteins are typically greater than 10 kDa to 1000 kDa and are more difficult to ionize as parent ions. To achieve quantitative mass spectral analysis, the proteins have to be broken into smaller fragments typically by proteolysis with enzymes like trypsin. However, the trypsinization reaction of proteins is not reproducible; not all proteins and bound forms can be fragmented; certain epitopes or forms of interest are fragmented and cannot be detected; and various components of the sample inhibit the activity of trypsin, for example. Another problem is that this peptide method often requires higher affinity antibodies than for a typical immunoassay. Another problem is that these fragments often do not relate to the clinical state as they are not the relevant molecule regions. It appears that this method of analysis remains a difficult and complex multistep process to automate and is noncompetitive with other detection technologies.

There is, therefore, a need to develop a method of detecting one or more different populations of rare molecules in a blood sample suspected of containing the one or more different populations of rare molecules and non-rare molecules while avoiding or reducing the problems associated with other approaches as set forth above.

SUMMARY

Some examples in accordance with the principles described herein are directed to methods of detecting one or more different populations of target rare molecules in a sample suspected of containing the one or more different populations of rare molecules and non-rare molecules. The concentration of the one or more different populations of target rare molecules is enhanced over that of the non-rare molecules to form a concentrated sample, which is incubated with, for each different population of target rare molecules, an affinity agent that comprises a specific binding partner that is specific for and binds to a target rare molecule of one of the populations of the target rare molecules. The affinity agent may be non-particulate or particulate and comprises a mass spectrometry (MS) label precursor or a first alteration agent, which either facilitates the formation of an MS label from the MS label precursor or releases an entity that comprises the MS label precursor from the affinity agent. The MS label corresponds to one of the populations of target rare molecules. A retentate and a filtrate are formed by contacting the incubated sample with a porous matrix. One or both of the retentate and the filtrate are subjected to a second alteration agent that facilitates the formation of a MS label from the MS label precursor from the affinity agent if the first alteration agent does not facilitate the formation of a MS label from the MS label precursor. One or both of the retentate and the filtrate are subjected to MS analysis to determine the presence and/or amount of each different MS label. The presence and/or amount of each different MS label are related to the presence and/or amount of each different population of target rare molecules in the sample.

Some examples in accordance with the principles described herein are directed to methods of detecting one or more different populations of target rare cells in a sample suspected of containing the one or more different populations of rare cells and non-rare cells. The concentration of each of the one or more different populations of target rare cells is enhanced over that of the non-rare cells to form a concentrated sample, which is incubated with, for each different population of target rare cells, an MS label precursor and an alteration agent that facilitates the formation of an MS label from the MS label precursor. Either the MS label precursor or the alteration agent is part of an affinity agent that is specific for a target rare cell of one of the populations of the target rare cells. Each different MS label corresponds to one of the populations of target rare cells. A retentate and a filtrate are formed by disposing the concentrated sample on a side of a porous matrix and applying vacuum or negative pressure to the disposed concentrated sample. One or both of the retentate and the filtrate are subjected to MS analysis to determine the presence and/or amount of each different MS label, and the presence and/or amount of each different MS label is related to the present and/or amount of each different population of target rare cells in the sample.

Some examples in accordance with the principles described herein are directed to methods of one or more different populations of target rare molecules in a sample suspected of containing the one or more different populations of rare molecules and non-rare molecules. The sample that has an enhanced concentration of the one or more different populations of target rare molecules over that of the non-rare molecules wherein the target rare molecules are in particulate form is incubated with, for each different population of target rare molecules, an affinity agent that comprises a specific binding partner that is specific for and binds to a target rare molecule of one of the populations of the target rare molecules. The affinity agent comprises an MS label precursor or a first alteration agent. For each different population of target rare molecules, the affinity agent comprises a particle reagent. The first alteration agent either facilitates the formation of an MS label from the MS label precursor or releases an entity that comprises the MS label precursor from the affinity agent. During the incubating, for each different population of target rare molecules, particle aggregates are formed from the particle reagent of the affinity agent. A retentate and a filtrate are formed by contacting the incubated samples with a porous matrix. One or both of the retentate and the filtrate are subjected to a second alteration agent that facilitates the formation of an MS label from the MS label precursor from the affinity agent for each different population of target rare molecules when the first alteration agent does not facilitate the formation of an MS label from the MS label precursor. One or both of the retentate and the filtrate are subjected to MS analysis to determine the presence and/or amount of each different MS label, and the presence and/or amount of each different MS label is related to the present and/or amount of each different population of non-cellular target rare molecules in the sample.

BRIEF DESCRIPTION OF THE DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION OF SPECIFIC EMBODIMENTS

General Discussion

Figure 1:
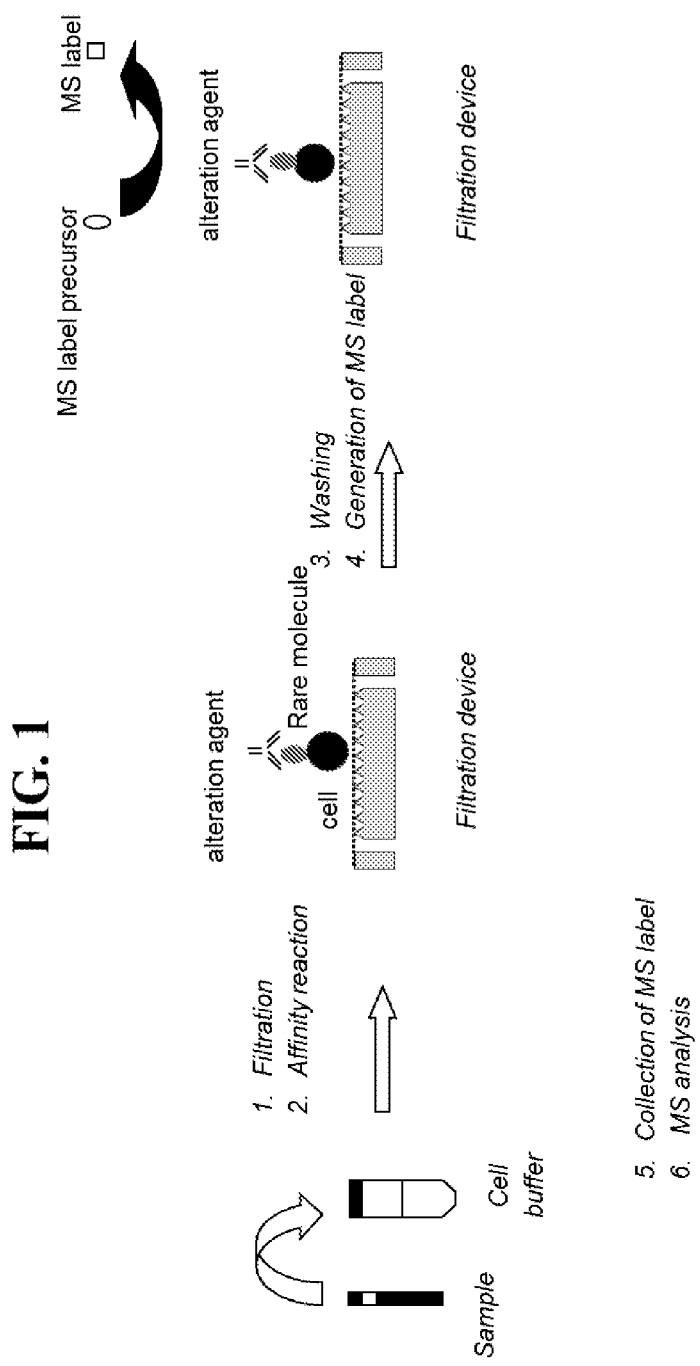
FIG. 1 is a schematic depicting an example of a method in accordance with the principles described herein for a target molecule that is associated with a cell and an alteration agent is attached to the affinity agent.

Examples in accordance with the principles described herein permit detection of different populations of target rare molecules employing affinity agents and different labels that are detectable using MS techniques. One or more alteration agents are used to generate MS labels that are chosen to differentiate among different populations of target rare molecules. The methods also employ separation methods that yield a retentate and a filtrate where one or both of the retentate and the filtrate are examined by MS techniques for one or both of the presence and amount of each different MS label. Differentiation of the MS labels yields information about one or both of the presence and amount of each different population of target rare molecules.

In one approach, particle amplification is utilized and provides for aggregating or clustering particles to form particle aggregates. In one example, a larger particle (carrier particle) can be coated by many smaller particles (label particles). To further achieve amplification in accordance with the principles described herein, the carrier particle can be chained with other carrier particles using a one or more linking group. The label particle contains the MS label on the surface, which may be on the order of $10^5$ since the size of mass label is comparatively small. In this approach, very low background levels are realized. Without being bound by any particular mechanism, carrier particles that do not bind to a target molecule apparently do not bind the surface of a membrane employed in a filtration device and are separated by passing through the pores of the membrane. In that regard, the carrier particles and label particles must have a diameter that is smaller than the pores in the filtration membrane.

Examples of methods in accordance with the principles described herein have benefits over known MS techniques as applied to the determination of rare cell populations and over microscopic detection techniques. For example, affinity reactions utilized in the methods in accordance with the principles described herein can be driven toward completion and a low background is provided particularly when a washing step is employed. Filtration in the methods in accordance with the principles described herein reduces the contribution of background and relatively large sample volumes can be used; high sensitivity is possible (e.g., 10 mL vs 10 µL) and the reaction can be driven into sub attomolar range. Simple filtration technology may be employed. Methods in accordance with the principles described herein are easily automatable. A single cell can be detected using methods in accordance with the principles described herein with low copy numbers of molecules. Methods in accordance with the principles described herein can be automated to a liquid format with very high MS sensitivity (to the fM level) and do not require and do not include trypsin digestion or additional pre-processing. This allows measuring the native forms of molecules of interest providing for clinically accurate measurements. Methods in accordance with the principles described herein allow use of recognized affinity agents. Normal antibodies can be used in methods in accordance with the principles described herein. Only one common standard is needed for all MS assays in the methods in accordance with the principles described herein, and no complex software is needed for interpretation of results. MS labels and MS label precursors may be chosen to avoid overlapping masses in MS detection and to avoid background interference problems. Furthermore, the use of one or more alteration agents and different MS label precursors allows for multiplexing, i.e., detection of multiple target rare molecules in one assay using MS label precursors that generate MS labels that are detectably different using MS techniques. Generic MS labels may be employed in the methods in accordance with the principles described herein.

Affinity agents can be multiplexed with separate MS label precursors or MS labels. When an enzyme is employed as an alteration agent, there is no need for sonication to remove the enzyme. Particle amplification in accordance with the principles described herein achieves very low background and high numbers of MS labels released for each different target rare molecule. Reactions can take place on a membrane of a filtration device and liquid may be removed by pipette to perform MS analysis.

Examples of Methods in Accordance with the Principles Described Herein

As mentioned above, some examples in accordance with the principles described herein are directed to methods of detecting one or more different populations of target rare molecules in a sample suspected of containing the one or more different populations of target rare molecules cells and non-rare molecules or cells. The sample to be analyzed is one that is suspected of containing target rare molecules, non-rare cells and rare cells. The samples may be biological samples or non-biological samples. Biological samples may be from a mammalian subject or a non-mammalian subject. Mammalian subjects may be, e.g., humans or other animal species. Biological samples include biological fluids such as whole blood, serum, plasma, sputum, lymphatic fluid, semen, vaginal mucus, feces, urine, spinal fluid, saliva, stool, cerebral spinal fluid, tears, and mucus, for example. Biological tissue includes, by way of illustration, hair, skin, sections or excised tissues from organs or other body parts, for example. In many instances, the sample is whole blood, plasma or serum. Rare cells may be from, for example, lung, bronchus, colon, rectum, pancreas, prostate, breast, liver, bile duct, bladder, ovary, brain, central nervous system, kidney, pelvis, uterine corpus, oral cavity or pharynx or melanoma cancers. The rare cells may be, but are not limited to, pathogens such as bacteria, virus, fungus, and protozoa; malignant cells such as malignant neoplasms or cancer cells; circulating endothelial cells; circulating tumor cells; circulating cancer stem cells; circulating cancer mesochymal cells; circulating epithelial cells; fetal cells; immune cells (B cells, T cells, macrophages, NK cells, monocytes); and stem cells; for example. In some examples of methods in accordance with the principles described herein, the sample to be tested is a blood sample from a mammal such as, but not limited to, a human subject, for example. The blood sample is one that contains cells such as, for example, non-rare cells and rare cells. In some examples the blood sample is whole blood or plasma.

The phrase "target rare molecule" refers to a molecule including biomarkers that may be detected in a sample where the molecule or biomarker is indicative of a particular population of cells. Target rare molecules include, but are not limited to, antigens (such as, for example, proteins, peptides, hormones, vitamins, allergens, autoimmune antigens, carbohydrates, lipids, glycoproteins, co-factors, antibodies, and enzymes) and nucleic acids, for example.

The phrase "population of target rare molecules" refers to a group of molecules that share a common antigen or nucleic acid that is specific for the group of molecules. The phrase "specific for" means that the common antigen or nucleic acid distinguishes the group of molecules from other molecules.

The phrase "population of cells" refers to a group of cells having an antigen or nucleic acid on their surface or inside the cell where the antigen is common to all of the cells of the group and where the antigen is specific for the group of cells.

Rare cells are those cells that are present in a sample in relatively small quantities when compared to the amount of non-rare cells in a sample. In some examples, the rare cells are present in an amount of about $10^{-8}$% to about $10^{-2}$% by weight of a total cell population in a sample suspected of containing the rare cells. The rare cells may be, but are not limited to, malignant cells such as malignant neoplasms or cancer cells; circulating endothelial cells; circulating epithelial cells; mesochymal cells; fetal cells; immune cells (B cells, T cells, macrophages, NK cells, monocytes); stem cells; nucleated red blood cells (normoblasts or erythroblasts); and immature granulocytes; for example.

Non-rare cells are those cells that are present in relatively large amounts when compared to the amount of rare cells in a sample. In some examples, the non-rare cells are at least about 10 times, or at least about $10^2$ times, or at least about $10^3$ times, or at least about $10^4$ times, or at least about $10^5$ times, or at least about $10^6$ times, or at least about $10^7$ times, or at least about $10^8$ times greater than the amount of the rare cells in the total cell population in a sample suspected of containing non-rare cells and rare cells. The non-rare cells may be, but are not limited to, white blood cells, platelets, and red blood cells, for example.

Target rare molecules of rare cells include, but are not limited to, cancer cell type biomarkers, oncoproteins and oncogenes, chemo resistance biomarkers, metastatic potential biomarkers, and cell typing markers, for example. Cancer cell type biomarkers include, by way of illustration and not limitation, cytokeratins (CK) (CK1, CK2, CK3, CK4, CKS, CK6, CK7, CK8 and CK9, CK10, CK12, CK 13, CK14, CK16, CK17, CK18, CK19 and CK2), epithelial cell adhesion molecule (EpCAM), N-cadherin, E-cadherin and vimentin, for example. Oncoproteins and oncogenes with likely therapeutic relevance due to mutations include, but are not limited to, WAF, BAX-1, PDGF, JAGGED 1, NOTCH, VEGF, VEGHR, CAIX, MIB1, MDM, PR, ER, SELS, SEM1, PI3K, AKT2, TWIST1, EML-4, DRAFF, C-MET, ABL1, EGFR, GNAS, MLH1, RET, MEK1, AKT1, ERBB2, HER2, HNF1A, MPL, SMAD4, ALK, ERBB4, HRAS, NOTCH1, SMARCB1, APC, FBXW7, IDH1, NPM1, SMO, ATM, FGFR1, JAK2, NRAS, SRC, BRAF, FGFR2, JAK3, RA, STK11, CDH1, FGFR3, KDR, PIK3CA, TP53, CDKN2A, FLT3, KIT, PTEN, VHL, CSF1R, GNA11, KRAS, PTPN11, DDR2, CTNNB1, GNAQ, MET, RB1, AKT1, BRAF, DDR2, MEK1, NRAS, FGFR1, and ROS1, for example.

Endothelial cell typing markers include, by way of illustration and not limitation, CD136, CD105/Endoglin, CD144/VE-cadherin, CD145, CD34, Cd41 CD136, CD34, CD90, CD31/PECAM-1, ESAM, VEGFR2/Fik-1, Tie-2, CD202b/TEK, CD56/NCAM, CD73/VAP-2, claudin 5, Z0-1, and vimentin, for example.

Metastatic potential biomarkers include, but are limited to, urokinase plasminogen activator (uPA), plasminogen activator inhibitor (PAI-1), CD95, serine proteases (e.g., plasmin and ADAM, for example); serine protease inhibitors (e.g., Bikunin); matrix metalloproteinases (e.g., MMP9); matrix metalloproteinase inhibitors (e.g., TIMP-1). Chemoresistance biomarkers include, by way of illustration and not limitation, PL2L piwi like, 5T4, ADLH, β-integrin, α6 integrin, c-kit, c-met, LIF-R, CXCR4, ESA, CD 20, CD44, CD133, CKS, TRAF2 and ABC transporters, cancer cells that lack CD45 or CD31 but contain CD34 are indicative of a cancer stem cell; and cancer cells that contain CD44 but lack CD24.

In methods in accordance with the principles described herein, white blood cells may be excluded as non-rare cells. For example, markers such as, but not limited to, CD45, CTLA-4, CD4, CD6S and CDS that are present on white blood cells can be used to indicate that a cell is not a rare cell of interest. In a particular non-limiting example, CD45 antigen (also known as protein tyrosine phosphatase receptor type C or PTPRC) and originally called leukocyte common antigen is useful in detecting all white blood cells.

Additionally, CD45 can be used to differentiate different types of white blood cells that might be considered rare cells. For example, granulocytes are indicated by CD45+, CD15+; monocytes are indicated by CD45+, CD14+; T lymphocytes are indicated by CD45+, CD3+; T helper cells are indicated by CD45+,CD3+, CD4+; cytotoxic T cells are indicated by CD45+,CD3+, CDS+; β-lymphocytes are indicated by CD45+, CD19+ or CD45+, CD20+; thrombocytes are indicated by CD45+, CD61+; and natural killer cells are indicated by CD16+, CD56+, and CD3−. Furthermore, two commonly used CD molecules, namely, CD4 and CD8, are, in general, used as markers for helper and cytotoxic T cells, respectively. These molecules are defined in combination with CD3+, as some other leukocytes also express these CD molecules (some macrophages express low levels of CD4; dendritic cells express high levels of CDS).

In other cases the rare cell is a pathogen, which includes, but is not limited to, gram-positive bacteria (e.g., *Enterococcus* sp. Group B *streptococcus*, Coagulase-negative *staphylococcus* sp. *Streptococcus viridans*, *Staphylococcus aureus* and *saprophyicus*, *Lactobacillus* and resistant strains thereof, for example); yeasts including, but not limited to, *Candida albicans*, for example; gram-negative bacteria such as, but not limited to, *Escherichia coli*, *Klebsiella pneumoniae*, *Citrobacter koseri*, *Citrobacter freundii*, *Klebsiella oxytoca*, *Morganella morganii*, *Pseudomonas aeruginosa*, *Proteus mirabilis*, *Serratia marcescens*, and Diphtheroids (gnb) and resistant strains thereof, for example; viruses such as, but not limited to, HIV, HPV, Flu, and MERSA, for example; and sexually transmitted diseases. In the case of detecting rare cell pathogens, a particle reagent is added that comprises a binding partner, which binds to the rare cell pathogen population. Additionally, for each population of cellular target rare molecules on the pathogen, a reagent is added that comprises a binding partner for the cellular target rare molecule, which binds to the cellular target rare molecules in the population.

The phrase "non-cellular target rare molecules" refers to target rare molecules that are not bound to a cell and/or that freely circulate in a sample. Such non-cellular target rare molecules include biomolecules useful in medical diagnosis of diseases, which include, but are not limited to, biomarkers for detection of cancer, cardiac damage, cardiovascular disease, neurological disease, hemostasis/hemastasis, fetal maternal assessment, fertility, bone status, hormone levels, vitamins, allergies, autoimmune diseases, hypertension, kidney disease, diabetes, liver diseases, infectious diseases and other biomolecules useful in medical diagnosis of diseases, for example.

As mentioned above, in some instances, one or more of the populations of target rare molecules may be a population of non-cellular target rare molecules. In such an instance, for each population of non-cellular target rare molecules, a capture particle entity is added that comprises a binding partner for the non-cellular target rare molecule, which binds to the non-cellular target rare molecules in the population to form particle-bound non-cellular target rare molecules thereby rendering a non-cellular target rare molecule in particulate form for purposes of carrying out an enhancement of a concentration of one or different populations of a non-cellular target rare molecule over that of non-rare molecules to form a concentrated sample in accordance with principles described herein.

The composition of the particle of the capture particle entity may be organic or inorganic, magnetic or non-magnetic. Organic polymers include, by way of illustration and not limitation, nitrocellulose, cellulose acetate, poly(vinyl chloride), polyacrylamide, polyacrylate, polyethylene, polypropylene, poly(4-methylbutene), polystyrene, poly(methyl methacrylate), poly(hydroxyethyl methacrylate), poly(styrene/divinylbenzene), poly(styrene/acrylate), poly(ethylene terephthalate), melamine resin, nylon, poly(vinyl butyrate), for example, either used by themselves or in conjunction with other materials and including latex, microparticle and nanoparticle forms thereof. The particles may also comprise carbon (e.g., carbon nanotubes), metal (e.g., gold, silver, and iron, including metal oxides thereof), colloids, dendrimers, dendrons, nucleic acids, Branch chain-DNA, and liposomes, for example.

The diameter of the particles of the particle entity is dependent on one or more of the nature of the target rare molecule, the nature of the sample, the nature and the pore size of a filtration matrix, the adhesion of the particle to matrix, the surface of the particle, the surface of the matrix, the liquid ionic strength, liquid surface tension and components in the liquid, and the number, size, shape and molecular structure of attached affinity agent and MS label precursors, for example. When a porous matrix is employed in filtration separation step, the diameter of the particles must be large enough to reduce background contribution to an acceptable level but not so large as to achieve inefficient separation of the particles from non-rare molecules. In some examples in accordance with the principles described herein, the average diameter of the particles should be at least about 0.02 microns (20 nm) and not more than about 200 microns, or not more than about 120 microns. In some examples, the particles have an average diameter from about 0.1 microns to about 20 microns, or about 0.1 microns to about 15 microns, or about 0.1 microns to about 10 microns, or about 0.02 microns to about 0.2 microns, or about 0.2 microns to about 1 micron, or about 1 micron to about 5 microns, or about 1 micron to about 20 microns, or about 1 micron to about 15 microns, or about 1 micron to about 10 microns, or about 5 microns to about 20 microns, or about 5 to about 15 microns, or about 5 to about 10 microns, or about 6 to about 15 microns, or about 6 to about 10 microns, for example. In some examples, the adhesion of the particles to the surface is so strong that the particle diameter can be smaller than the pore size of the matrix. In other examples, the particles are sufficiently larger than the pore size of the matrix such that physically the particles cannot fall through the pores.

The capture particle entity also includes a binding partner that is specific for the non-cellular target rare molecule. The phrase "binding partner" refers to a molecule that is a member of a specific binding pair. A member of a specific binding pair is one of two different molecules having an area on the surface or in a cavity, which specifically binds to and is thereby defined as complementary with a particular spatial and polar organization of the other molecule. The members of the specific binding pair may be members of an immunological pair such as antigen-antibody or hapten-antibody, biotin-avidin, hormones-hormone receptors, enzyme-substrate, nucleic acid duplexes, IgG-protein A, and polynucleotide pairs such as DNA-DNA, DNA-RNA, for example. The binding partner may be bound, either covalently or non-covalently, to the particle of the particle reagent. "Non-covalently" means that the binding partner is bound to the particle as the result of one or more of hydrogen bonding, van der Waals forces, electrostatic forces, hydrophobic effects, physical entrapment in the particles, and charged interactions, for example. "Covalently" means that the binding partner is bound to the particle by a bond or a linking group, which may be aliphatic or aromatic and may comprise a chain of 2 to about 60 or more atoms that include carbon, oxygen, sulfur, nitrogen and phosphorus.

In some examples in accordance with the principles described herein, samples are collected from the body of a subject into a suitable container such as, but not limited to, a cup, a bag, a bottle, capillary, or a needle, for example. Blood samples may be collected into VACUTAINER® containers, for example. The container may contain a collection medium into which the sample is delivered. The collection medium is usually a dry medium and may comprise an amount of platelet deactivation agent effective to achieve deactivation of platelets in the blood sample when mixed with the blood sample.

Platelet deactivation agents include, but are not limited to, chelating agents such as, for example, chelating agents that comprise a triacetic acid moiety or a salt thereof, a tetraacetic acid moiety or a salt thereof, a pentaacetic acid moiety or a salt thereof, or a hexaacetic acid moiety or a salt thereof. In some examples, the chelating agent is ethylene diamine tetraacetic acid (EDTA) and its salts or ethylene glycol tetraacetate (EGTA) and its salts. The effective amount of platelet deactivation agent is dependent on one or more of the nature of the platelet deactivation agent, the nature of the blood sample, level of platelet activation and ionic strength, for example. In some examples, for EDTA as the anti-platelet agent, the amount of dry EDTA in the container is that which will produce a concentration of about 1.0 to about 2.0 mg/mL of blood, or about 1.5 mg/mL of the blood. The amount of the platelet deactivation agent is that which is sufficient to achieve at least about 90%, or at least about 95%, or at least about 99% of platelet deactivation.

In methods in accordance with the principles described herein, the concentration of the one or more different populations of target rare molecules is enhanced over that of the non-rare molecules to form a concentrated sample. In some examples, the sample is subjected to a filtration procedure using a porous matrix that retains the target rare molecules while allowing the non-rare molecules to pass through the porous matrix thereby enhancing the concentration of the target rare molecules. In the event that one or more target rare molecules are non-cellular, i.e., not associated with a cell or other biological particle, the sample is combined with one or more capture particle entities wherein each capture particle entity comprises a binding partner for the non-cellular target rare molecule of each of the populations of non-cellular target rare molecules to render the non-cellular target rare molecules in particulate form, i.e., to form particle-bound non-cellular target rare molecules. The combination of the sample and the capture particle entities is held for a period of time and at a temperature to permit the binding of non-cellular target rare molecules with corresponding binding partners of the capture particle entities. Moderate temperatures are normally employed, which may range from about 5° C. to about 70° C. or from about 15° C. to about 70° C. or from about 20° C. to about 45° C., for example. The time period for an incubation period is about 0.2 seconds to about 6 hours, or about 2 seconds to about 1 hour, or about 1 to about 5 minutes, for example.

The porous matrix of the filtration device is a solid or semi-solid material and may be comprised of an organic or inorganic, water insoluble material. The porous matrix can have any of a number of shapes such as, for example, tubular (e.g., hollow fiber, spiral wound, and hollow fine fiber), track-etched, or planar or flat surface (e.g., strip, disk, film, membrane, and plate). The matrix may be fabricated from a wide variety of materials, which may be naturally occurring or synthetic, polymeric or non-polymeric, fibrous or non-fibrous. The porous matrix can be produced by microelectromechanical (MEMS) technology, metal oxide semiconductor (CMOS) technology or micro-manufacturing processes for producing microsieves. Examples, by way of illustration and not limitation, of such materials for fabricating a porous matrix include cellulose (including paper), nitrocellulose, cellulose acetate, polycarbonate, poly (vinyl chloride), polyacrylamide, polyacrylate, polyethylene, polypropylene, poly-(4-methylbutene), polystyrene, polymethacrylate, poly(ethylene terephthalate), polysulfone, nylon, parylene, silicon, poly(vinyl butyrate), ceramic material, and metallic material, for example, either used by themselves or in conjunction with one another and/or with other materials.

In some examples, the size of the pores of a porous matrix is that which is sufficient to preferentially retain certain cells and/or particle reagents while allowing the passage of other cells or particles through the pores and not clog the pores of the porous matrix. The size of the pores of the porous matrix is dependent on one or more of the nature and size of the different populations of target rare cells, the nature and size of particle reagents used for non-cellular target rare molecules, the nature and size of non-rare cells, the vacuum applied to the sample on the porous matrix, the size of the components in the sample that are to be washed through, the size of non-rare cells in sample, and the size of plasma proteins in sample, if any, for example. In some examples the average size of the pores of the porous matrix is about 1 μm to about 100 μm, or about 1 μm to about 75 μm, or about 1 μm to about 50 μm, or about 1 μm to about 20 μm, or about 1 μm to about 10 μm, or about 5 μm to about 100 μm, or about 5 μm to about 75 μm, or about 5 μm to about 50 μm, or about 5 μm to about 20 μm, or about 5 μm to about 10 μm, for example. The density of pores in the porous matrix is about 1% to about 80%, or about 10% to about 80%, or about 20% to about 80%, or about 50% to about 80%, or about 20% to about 70%, for example.

In some examples, vacuum is applied to the sample on the porous matrix to facilitate passage of non-rare cells and other particles through the membrane. The level of vacuum applied is dependent on one or more of the nature and size of the different populations of rare cells and/or particle reagents, the nature of the porous matrix, and the size of the pores of the porous matrix, for example. In some examples, the level of vacuum applied is about 1 millibar to about 100 millibar, or about 1 millibar to about 80 millibar, or about 1 millibar to about 50 millibar, or about 1 millibar to about 40 millibar, or about 1 millibar to about 30 millibar, or about 1 millibar to about 25 millibar, or about 1 millibar to about 20 millibar, or about 1 millibar to about 15 millibar, or about 1 millibar to about 10 millibar, or about 5 millibar to about 100 millibar, or about 5 millibar to about 80 millibar, or about 5 millibar to about 50 millibar, or about 5 millibar to about 30 millibar, or about 5 millibar to about 25 millibar, or about 5 millibar to about 20 millibar, or about 5 millibar to about 15 millibar, or about 5 millibar to about 10 millibar, for example. In some examples the vacuum is an oscillating vacuum, which means that the vacuum is applied intermittently at regular of irregular intervals, which may be, for example, about 1 second to about 600 seconds, or about 1 second to about 500 seconds, or about 1 second to about 250 seconds, or about 1 second to about 100 seconds, or about 1 second to about 50 seconds, or about 10 seconds to about 600 seconds, or about 10 seconds to about 500 seconds, or about 10 seconds to about 250 seconds, or about 10 seconds to about 100 seconds, or about 10 seconds to about 50 seconds, or about 100 seconds to about 600 seconds, or about 100 seconds to about 500 seconds, or about 100 seconds to about 250 seconds, for example. In this approach, vacuum is oscillated at about 0 millibar to about 10 millibar, or about 1 millibar to about 10 millibar, or about 1 millibar to about 7.5 millibar, or about 1 millibar to about 5.0 millibar, or about 1 millibar to about 2.5 millibar, for example, during some or all of the application of vacuum to the blood sample. Oscillating vacuum is achieved using an on-off switch, for example, and may be conducted automatically or manually.

Contact of the sample with the porous matrix is continued for a period of time sufficient to achieve retention of cellular target rare molecules and/or particle-bound non-cellular target rare molecules on a surface of the porous matrix to obtain a surface of the porous matrix having different populations of target rare cells and/or particle-bound target rare molecules as discussed above. The period of time is dependent on one or more of the nature and size of the different populations of target rare cells and/or particle-bound target rare molecules, the nature of the porous matrix, the size of the pores of the porous matrix, the level of vacuum applied to the blood sample on the porous matrix, the volume to be filtered, and the surface area of the porous matrix, for example. In some examples, the period of contact is about 1 minute to about 1 hour, about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes, for example.

In methods in accordance with the principles described herein, the concentrated sample is incubated with, for each different population of target rare molecules, an affinity agent that comprises a specific binding partner that is specific for and binds to a target rare molecule of one of the populations of the target rare molecules. The affinity agent also comprises an MS label precursor or a first alteration agent that facilitates the formation of an MS label from each different MS label precursor or that releases an entity that comprises the MS label precursor from the affinity agent. In many examples, the above combination is provided in an aqueous medium, which may be solely water or which may also contain organic solvents such as, for example, polar aprotic solvents, polar protic solvents such as, e.g., dimethylsulfoxide (DMSO), dimethylformamide (DMF), acetonitrile, an organic acid, or an alcohol, and non-polar solvents miscible with water such as, e.g., dioxene, in an amount of about 0.1% to about 50%, or about 1% to about 50%, or about 5% to about 50%, or about 1% to about 40%, or about 1% to about 30%, or about 1% to about 20%, or about 1% to about 10%, or about 5% to about 40%, or about 5% to about 30%, or about 5% to about 20%, or about 5% to about 10%, by volume. In some examples, the pH for the aqueous medium is usually a moderate pH. In some examples the pH of the aqueous medium is about 5 to about 8, or about 6 to about 8, or about 7 to about 8, or about 5 to about 7, or about 6 to about 7, or physiological pH, for example. Various buffers may be used to achieve the desired pH and maintain the pH during any incubation period. Illustrative buffers include, but are not limited to, borate, phosphate (e.g., phosphate buffered saline), carbonate, TRIS, barbital, PIPES, HEPES, MES, ACES, MOPS, and BICINE, for example.

An amount of aqueous medium employed is dependent on a number of factors such as, but not limited to, the nature and amount of the sample, the nature and amount of the reagents, the stability of target rare cells, and the stability of target rare molecules, for example. In some examples in accordance with the principles described herein, the amount of aqueous medium per 10 mL of sample is about 5 mL to about 100 mL, or about 5 mL to about 80 mL, or about 5 mL to about 60 mL, or about 5 mL to about 50 mL, or about 5 mL to about 30 mL, or about 5 mL to about 20 mL, or about 5 mL to about 10 mL, or about 10 mL to about 100 mL, or about 10 mL to about 80 mL, or about 10 mL to about 60 mL, or about 10 mL to about 50 mL, or about 10 mL to about 30 mL, or about 10 mL to about 20 mL, or about 20 mL to about 100 mL, or about 20 mL to about 80 mL, or about 20 mL to about 60 mL, or about 20 mL to about 50 mL, or about 20 mL to about 30 mL, for example.

Where one or more of the target rare molecules are part of a cell, the aqueous medium may also comprise a lysing agent for lysing of cells. A lysing agent is a compound or mixture of compounds that disrupt the integrity of the membranes of cells thereby releasing intracellular contents of the cells. Examples of lysing agents include, but are not limited to, non-ionic detergents, anionic detergents, amphoteric detergents, low ionic strength aqueous solutions (hypotonic solutions), bacterial agents, aliphatic aldehydes, and antibodies that cause complement dependent lysis, for example. Various ancillary materials may be present in the dilution medium. All of the materials in the aqueous medium are present in a concentration or amount sufficient to achieve the desired effect or function.

In some examples, where one or more of the target rare molecules are part of a cell, it may be desirable to fix the cells of the sample. Fixation of the cells immobilizes the cells and preserves cell structure and maintains the cells in a condition that closely resembles the cells in an in vivo-like condition and one in which the antigens of interest are able to be recognized by a specific affinity agent. The amount of fixative employed is that which preserves the cells but does not lead to erroneous results in a subsequent assay. The amount of fixative depends on one or more of the nature of the fixative and the nature of the cells, for example. In some examples, the amount of fixative is about 0.05% to about 0.15% or about 0.05% to about 0.10%, or about 0.10% to about 0.15%, for example, by weight. Agents for carrying out fixation of the cells include, but are not limited to, cross-linking agents such as, for example, an aldehyde reagent (such as, e.g., formaldehyde, glutaraldehyde, and paraformaldehyde); an alcohol (such as, e.g., C1-C5 alcohols such as methanol, ethanol and isopropanol); a ketone (such as a C3-C5 ketone such as acetone); for example. The designations C1-C5 or C3-C5 refer to the number of carbon atoms in the alcohol or ketone. One or more washing steps may be carried out on the fixed cells using a buffered aqueous medium.

If necessary after fixation, the cell preparation is also subjected to permeabilization. In some instances, a fixation agent such as, for example, an alcohol (e.g., methanol or ethanol) or a ketone (e.g., acetone) also results in permeabilization and no additional permeabilization step is necessary. Permeabilization provides access through the cell membrane to target molecules of interest. The amount of permeabilization agent employed is that which disrupts the cell membrane and permits access to the target molecules.

The amount of permeabilization agent depends on one or more of the nature of the permeabilization agent and the nature and amount of the cells, for example. In some examples, the amount of permeabilization agent is about 0.01% to about 10%, or about 0.1% to about 10%, for example. Agents for carrying out permeabilization of the cells include, but are not limited to, an alcohol (such as, e.g., C1-C5 alcohols such as methanol and ethanol); a ketone (such as a C3-C5 ketone such as acetone); a detergent (such as, e.g., saponin, TRITON® X-100, and TWEEN®-20); for example. One or more washing steps may be carried out on the permeabilized cells using a buffered aqueous medium.

As mentioned above, an affinity agent employed in methods in accordance with the principles described herein is one that is specific for a target rare molecule. The affinity agent is a member of a specific binding pair, which is one of two different molecules, having an area on the surface or in a cavity, which specifically binds to and is thereby defined as complementary with a particular spatial and polar organization of the other molecule. The members of the specific binding pair may be members of an immunological pair such as antigen-antibody and hapten-antibody, although other specific binding pairs include, for example, biotin-avidin, hormones-hormone receptors, enzyme-substrate, aptamers, nucleic acid duplexes, IgG-protein A, and nucleic acid pairs such as DNA-DNA, DNA-RNA. In the case of cells, the affinity agent is an agent that specifically recognizes or binds to a target molecule antigen associated with a cell.

Specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules.

Antibodies specific for a target molecule for use in immunoassays to identify cells can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, and Fab', for example. In addition, aggregates, polymers, and conjugates of immunoglobulins or their fragments can be used where appropriate so long as binding affinity for a particular molecule is maintained.

Polyclonal antibodies and monoclonal antibodies may be prepared by techniques that are well known in the art. For example, in one approach monoclonal antibodies are obtained by somatic cell hybridization techniques. Monoclonal antibodies may be produced according to the standard techniques of Köhler and Milstein, *Nature* 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981). In general, monoclonal antibodies can be purified by known techniques such as, but not limited to, chromatography, e.g., DEAE chromatography, ABx chromatography, and HPLC chromatography; and filtration, for example.

The affinity agent may be a nucleic acid (e.g., polynucleotide) that is complementary to a target nucleic acid. Polynucleotides refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides such as, for example, methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component.

The affinity agent comprises either an MS label precursor or an alteration agent that facilitates the formation of an MS label from an MS label precursor where the MS label corresponds to a target rare molecule of one of the populations of target rare molecules. The MS label allows differentiation of one of the populations of target rare molecules from other populations of rare molecules. Furthermore, selection of the MS label may be carried out to avoid overlapping masses in the analysis by MS, to avoid background interference in the MS analysis, and to permit multiplexing.

The phrase "mass spectrometry label" or "MS label" refers to a group of molecules having unique masses below 3 kDA such that each unique mass, corresponds to, and is used to determine a presence and/or amount of, each different population of target rare molecules. The MS labels are molecules of defined mass and include, but are not limited to, polypeptides, polymers, fatty acids, carbohydrates, organic amines, nucleic acids, and organic alcohols, for example, whose mass can be varied by substitution and chain size, for example. In the case of polymeric materials, the number repeating units is adjusted such that the mass is in a region that does not overlap with a background mass from the sample. The MS label generates a unique mass pattern due to structure and fragmentation upon ionization.

The "MS label precursor" is any molecule that results in an MS label by the action of the alteration agent. The MS label precursor may itself be an MS label that, through the action of the alteration agent is converted to another MS label by cleavage, by reaction with a moiety, by derivatization, or by addition or by subtraction of molecules, charges or atoms, for example, or a combination of two or more of the above.

The term "alteration agent" refers to a substance or ionization that in one example has the ability to alter the MS label precursor in accordance with the principles described herein to achieve an MS label having a unique mass in the range of about 1 Da to about 3 kDa, or in the range of about 1 Da to about 50 Da, or in the range of about 50 Da, to about 150 Da, or in the range of about 150 Da to about 700 Da, or in the range of about 700 Da to about 3 kDa, for example. In some examples the unique mass of the MS label is below about 3 kDa. The MS label precursor can be altered by bond breaking to form a neutral, negative or positive ion, or radical. The alteration of the MS label precursor by the alteration agent may be by addition of atoms, charges or electrons to, or subtraction of atoms, charges or electrons from, the MS label precursor or by bond cleavage in, or bond formation in, the MS label precursor. The alteration agents include, but are not limited to, chemical agents such as, but not limited to, catalysts (e.g., enzymes (including pseudoenzymes) and metals), oxidizing agents, reducing agents, acids, bases, agents that promote substitution reactions or replacement reactions; and ionization agents; for example. In some examples, the alteration agent facilitates the formation of an MS label from the MS label precursor by promoting the reaction of the MS label precursor with a moiety to form the MS label, for example. In some examples the alteration agent facilitates the formation of an MS label from the MS label precursor by promoting the release of the MS label from the MS label precursor, for example.

The nature of the MS label precursors is dependent on one or more of the nature of the MS label, the nature of the MS method employed, the nature of the MS detector employed, the nature of the target rare molecules, the nature of the affinity agent, the nature of any immunoassay employed, the nature of the sample, the nature of any buffer employed, the nature of the separation, for example. In some examples, the MS label precursors are molecules whose mass can be varied by substitution and/or chain size. The MS labels produced from the MS label precursors are molecules of defined mass, which should not be present in the sample to be analyzed. Furthermore, the MS labels should be in the range detected by the MS detector, should not have overlapping masses and should be detectable by primary mass. Examples, by way of illustration and not limitation, of MS label precursors for use in methods in accordance with the principles described herein to produce MS labels include, by way of illustration and not limitation, polypeptides, organic and inorganic polymers, fatty acids, carbohydrates, cyclic hydrocarbons, aliphatic hydrocarbons, aromatic hydrocarbons, organic carboxylic acids, organic amines, nucleic acids, organic alcohols (e.g., alkyl alcohols, acyl alcohols, phenols, polyols (e.g., glycols), thiols, epoxides, primary, secondary and tertiary amines, indoles, tertiary and quaternary ammonium compounds, amino alcohols, amino thiols, phenolic amines, indole carboxylic acids, phenolic acids, vinylogous acid, carboxylic acid esters, phosphate esters, carboxylic acid amides, carboxylic acids from polyamides and polyesters, hydrazone, oxime, trimethylsilyl enol ether, acetal, ketal, carbamates, ureas, guanidines, isocyanates, sulfonic acids, sulfonamides, sulfonylureas, sulfates esters, monoglycerides, glycerol ethers, sphingosine bases, ceramines, cerebrosides, steroids, prostaglandins, carbohydrates, nucleosides and therapeutic drugs, for example.

An MS label precursor can include 1 to about 100,000 MS labels, or about 10 to about 100,000 MS labels, or about 100 to about 100,000 MS labels, or about 1,000 to about 100,000 MS labels, or about 10,000 to about 100,000 MS labels, for example. The MS label precursor can be comprised of proteins, polypeptides, polymers, particles, carbohydrates, nucleic acids, lipids or other macromolecules capable of including multiple repeating units of MS labels by attachment. Multiple MS labels allow amplification as every MS label precursor can generate many MS labels.

With polypeptide MS label precursors, for example, the chain length of the polypeptide can be adjusted to yield an MS label in a mass region without background peaks. Furthermore, MS labels may be produced from the MS label precursors having unique masses, which are not present in the sample tested. The polypeptide MS label precursors can comprise additional amino acids or derivatized amino acids, which allows methods in accordance with the principles described herein to be multiplexed to obtain more than one result at a time. Examples of polypeptide MS label precursors include, but are not limited to, polyglycine, polyalanine, polyserine, polythreonine, polycysteine, polyvaline, polyleucine, polyisoleucine, polymethionine, polyproline, polyphenylalanine, polytyrosine, polytryptophan, polyaspartic acid, polyglutamic acid, polyasparagine, polyglutamine, polyhistidine, polylysine and polyarginine, for example. Polypeptide MS label precursors differentiated by mixtures of amino acids or derivatized amino acids generate masses having even or odd election ion with or without radicals. In some examples, polypeptides are able to be modified by catalysis. For example, by way of illustration and not limitation, phenol and aromatic amines can be added to polythreonine using a peroxidase enzyme as a catalyst. In another example, by way of illustration and not limitation, electrons can be transferred to aromatic amines using peroxidase enzyme as a catalyst. In another example, by way of illustration and not limitation, phosphates can be removed from organic phosphates using phosphatases as a catalyst.

In another example, by way of illustration and not limitation, a derivatization agent is employed as a moiety to generate an MS label from an MS label precursor. For example, dinitrophenyl and other nitrophenyl derivatives may be formed from the MS label precursor. Other examples include, by way of illustration and not limitation, esterification, acylation, silylation, protective alkylation, derivatization by ketone-base condensations such as Schiff bases, cyclization, formation of fluorescent derivatives, and inorganic anions. The derivatization reactions can occur in microreaction prior to MS analysis but after affinity reaction or be used to generate MS label precursors conjugated to affinity reagents.

In some examples in accordance with the principles described herein, the MS label precursor can comprise an isotope such as, but not limited to, $^2H$, $^{13}C$, and $^{18}O$, for example, which remains in the MS label that is derived from the MS label precursor. The MS label can be detected by the primary mass or a secondary mass after ionization. In some examples, the MS label precursor is one that has a relatively high potential to cause a bond cleavage such as, but not limited to, alkylated amines, acetals, primary amines and amides, for example, where the MS label can generate a mass that has even or odd election ion with or without radicals. Selection of the polypeptide can generate a unique MS spectral signature.

As mentioned above, the alteration agent may be an enzyme (which includes pseudoenzymes). In some examples, catalysis can occur with water insoluble enzyme derivatives immobilized with, for example, silica gels, charcoals, DEAE-cellulose, DEAE-SEPHADEX, cellulose citrate, kaolinite, cellulose phosphate, acid clay, AMBERLITE XE-97, carboxymethyl cellulose, glass, quartz, dowex-50, starch gel, polyacrylamide gel, poly amino acids, or aminobenzyl cellulose. Cross-linking agents can be used to immobilize the enzyme. Such cross-linking agents include, but are not limited to, glutaraldehyde, dimethyl adipimidate, carbodiimide, maleic anhydride, MDA methylenedianiline, hydrazide, and acyl azides, for example.

In some examples, an enzyme for purposes in accordance with the principles described herein is any enzyme with a high turnover rate that can convert as an enzyme substrate (such as an MS label precursor) into an MS label that is detected by the mass detector of a mass spectrometer in the presence of the un-converted substrate. The enzyme should not be in the sample tested or, if present in the sample, it must be removed from the sample prior to testing. Examples of enzymes suitable for this purpose include, but are not limited to, phosphatases (e.g., alkaline phosphatase, lipid phosphatases, tyrosine phosphatase, serine phosphatase, threonine phosphatase, and histidine phosphatase); oxidases (e.g., horse radish peroxidase, copper amine oxidase, D-amino acid oxidase, galactose oxidase, plasma amine oxidase, tryptophan peroxidase, uricase oxidase, and xanthine oxidase); β-galactosidase; transferases (e.g., D-alanine transferase, glycosyl transferase, acyl transferase, alkyl transferase, aryl transferase, single carbon transferase, ketone transferase, aldehyde transferase, nitrogenous transferase, phosphorus transferase, sulfur transferase, and pentosyl transferase); peptidases (e.g., pepsin, papain, rennin (chymosin), renin, thrombin, trypsin, matrix metallopeptidase, cathespin, cysteine protease, and carboxypeptidase); aldolases (e.g., carboxyl aldolase, aldehyde aldolase, oxo acids, tryptophanase); fatty acid enzymes (e.g., fatty acid amine hydrolase, fatty acid synthase, and choline acetyltransferase), for example, and combinations of two or more of the above (e.g., two or more of alkaline phosphatase, acid phosphatase, an oxidase, β-galactosidase, peroxidase, acylase, asparaginase, catalase, chymotrypsin, amylase, glucoamylase, glucose oxidase, glucose-6-phosphate dehydrogenase, hexokinase, invertase, lipase, phosphoglucomutase, ribonuclease, acetylcholinesterase, alcohol dehydrogenase, aldolase, cholinesterase, citrate synthetase, urease, amylglucosidase, carboxypeptidase, cholinesterase, luciferase, ribonuclease, pyruvate kinase, and subtilopeptidase).

Substrates for the enzymes are MS label precursors that comprise an MS label that is released by the action of the enzyme on the substrate. Such MS labels that may be part of an enzyme substrate include, by way of illustration and not limitation, phenols (from substrates such as, for example, p-nitrophenyl phosphate, p-nitrophenyl-β-D-galactoside, amino acids, peptides, carbohydrates (6-phospho-D-gluconate), fatty acids (acetyl-CoA), alkyl amines, glycerols); and naphthols (from substrates such as, for example, p-nitronaphthyl phosphate, p-nitro-naphthyl-β-D-galactoside); for example.

Metals that may be employed to release an MS label from a moiety attached to an affinity agent include, but are not limited to, transition metals (e.g., palladium, platinum, gold, ruthenium, rhodium, or iridium), chelated metals (e.g., iron, copper, cobalt, magnesium complexed by ethylenediaminetetraacetate (EDTA), N-(2-hydroxyethyl)-ethylenediaminetriacetic acid (HEDTA), or trans-1,2-cyclohexanediaminetetraacetic acid (CDTA), for example), metal oxidants (e.g., sodium hypochlorite, potassium periodate, silver oxide, chromic acid, potassium permanganate, and sodium perborate) and metal reductants (e.g., lithium aluminum hydride, sodium borohydride, sodium ascorbate, phosphites, and sodium), for example.

Examples, by way of illustration and not limitation, of MS label groups are set forth in Table 1.

TABLE 1

| Structure Name | Structure | Molecular Weight |
| --- | --- | --- |
| 3-O-Tolyloxymethyl-piperidine | 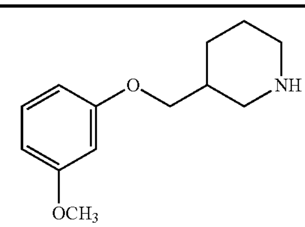 | 205.3 |
| Poly(ethylene glycol)methyl ether amine | 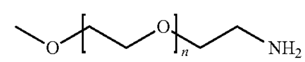 | Average 500 |
| 3,3'-Iminopropionitrile | 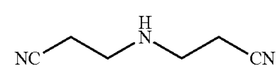 | 123.2 |
| 3,6-Di-o-(tert-Butyldiphenylsilyl)-D-galactal | 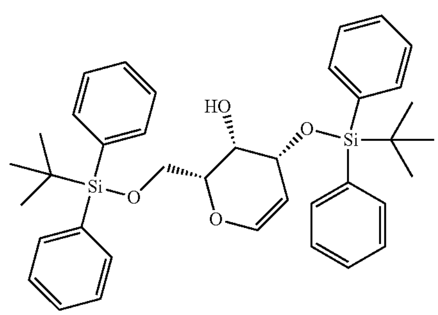 [SMILES: CC(C)(C)[Si](OC[C@H]1OC=C[C@@H](O[Si](c2ccccc2)(c2ccccc2)C(C)(C)C)[C@H]1O)(c1ccccc1)c1ccccc1] | 622.9 |
| 4-Bromobenzaldehyde diethyl acetal | 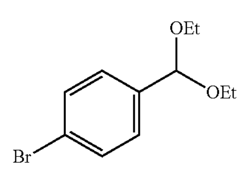 [SMILES: CCOC(OCC)c1ccc(Br)cc1] | 259.1 |

TABLE 1-continued

| Structure Name | Structure | Molecular Weight |
|---|---|---|
| Benzyl-(2-fluoro-benzyl) amine | 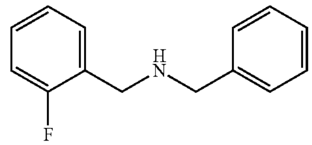 [SMILES: Fc1ccccc1CNCc1ccccc1] | 215.3 |
| 2,2-dimethoxy-2-phenylacetophenone | 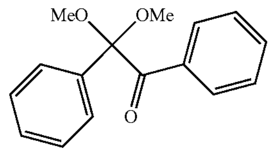 [SMILES: COC(OC)(C(=O)c1ccccc1)c1ccccc1] | 256.3 |
| 4-(3-methoxypropyl) piperidine | 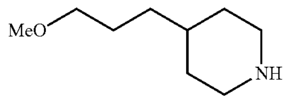 [SMILES: COCCCC1CCNCC1] | 157.3 |
| (2-ethoxybutly) amine | 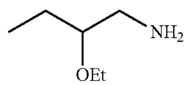 | 117.2 |
| 4-(2-methoxyphenylsulfanyl) piperidine | 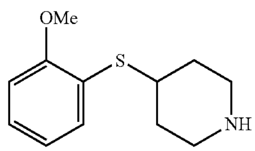 [SMILES: COc1ccccc1SC1CCNCC1] | 223.3 |
| 2-(Isopropylsulfonyl)ethanamine | 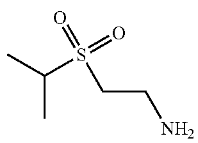 | 151.1 |
| 3-Iodobenzylamine | 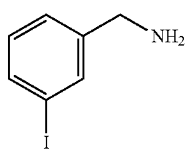 | 233.1 |
| (3,5-dimethyl-4-methylsulfanyl-phenyl) N-methylcarbamate Mercaptodimethur | 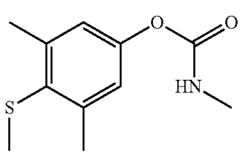 | 225.3 |
| 3,4-Dibenzyloxyphenethylamine | 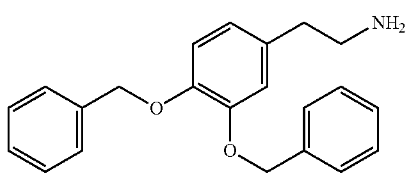 [SMILES: NCCc1ccc(OCc2ccccc2)c(OCc2ccccc2)c1] | 333.4 |
| methyl N-[[2-chloro-5-[(Z)-C-methyl-N-[(6-methyl-2-pyridyl) methoxy]carbonimidoyl]phenyl] methyl]carbamate Z-Pyribencarb | 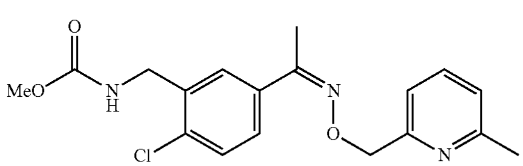 [SMILES: COC(=O)NCc1cc(/C(C)=N\OCc2cccc(C)n2)ccc1Cl] | 361.8 |

TABLE 1-continued

| Structure Name | Structure | Molecular Weight |
|---|---|---|
| Nile blue | 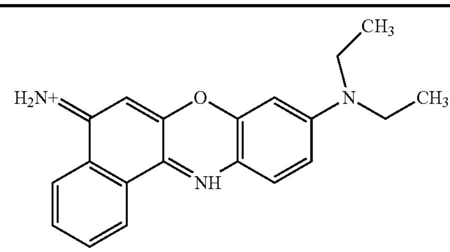 | 353.8 |
| 9-diethylamino-5-benzo[α]phenoxazinone (Nile red) | 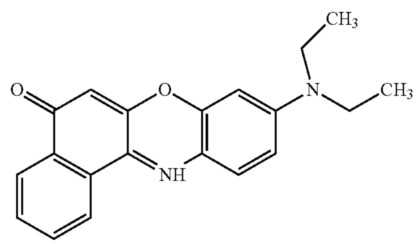 [SMILES: CCN(CC)c1ccc2nc3c4ccccc4c(=O)cc-3oc2c1] | 318.4 |
| Cysteamine Nile blue | 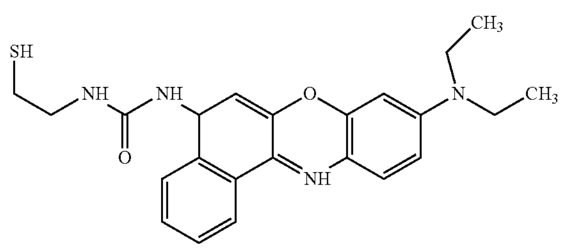 [SMILES: CCN(CC)c1ccc2c(c1)OC1=CC(NC(=O)NCCS)c3ccccc3C1=N2] | |

The MS label can be detected directly or the released MS label can be further reacted with another compound to form a derivative MS label, which is detected by MS techniques. A derivative MS label is a compound that is formed from an MS label that is obtained from the MS label precursor where the compound also is detectable by MS techniques. This approach of forming a derivate MS label further enhances the multiplexing capability of methods in accordance with the principles described herein. For example, a released phenol or naphthol can couple to an aromatic amine in the presence of a peroxidase (see, for example, U.S. Pat. No. 5,182,213, the relevant disclosure of which is incorporated herein by reference). In one example, a released naphthol is coupled with a phenylenediamine such as, for example, α-phenylenediamine dihydrochloride, in the presence of a peroxidatively active substance in an alkaline medium to produce a derivative MS label. Multiplexing may be achieved using different naphthols and/or different phenylenediamines.

Internal standards are an important aspect of mass spectral analysis. In some examples, a second mass label can be added that can be measured (as an internal standard) in addition to the MS label used for detection of the rare target molecule. The internal standard has a similar structure to the MS label with a slight shift in mass. The internal standards can be prepared that comprise additional amino acids or derivatized amino acids. Alternatively, the internal standard can be prepared by incorporating an isotopic label such as, but not limited to $^2H$ (D), $^{13}C$, and $^{18}O$, for example. The MS isotope label has a mass higher than the naturally-occurring substance. For example, the isotope labeled MS labels, for example, glycerol-C-d7, sodium acetate-C-d7, sodium pyruvate-C-d7, D-glucose-C-d7, deuterated glucose, and dextrose-C-d7, would serve as internal standards for glycerol, sodium acetate, sodium pyruvate, glucose and dextrose, respectively.

An MS label precursor or an alteration agent may be attached to an affinity agent (to yield a modified affinity agent) covalently either directly by a bond or through the intermediacy of a linking group. In some embodiments the preparation of a modified affinity agent may be carried out by employing functional groups suitable for attaching the MS label precursor or the alteration agent, to the affinity agent by a direct bond. The nature of the functional groups employed is dependent, for example, on one or more of the nature of the MS label precursor, the nature of the alteration agent, and the nature of the affinity agent including the nature of one or more different particles such as, e.g., carrier particles and label particles that may be part of the affinity agent. A large number of suitable functional groups are available for attaching to amino groups and alcohols; such functional groups include, for example, activated esters including, e.g., carboxylic esters, imidic esters, sulfonic esters and phosphate esters; activated nitrites; aldehydes; ketones; and alkylating agents.

The linking group may be a chain of from 1 to about 60 or more atoms, or from 1 to about 50 atoms, or from 1 to about 40 atoms, or from 1 to 30 atoms, or from about 1 to about 20 atoms, or from about 1 to about 10 atoms, each independently selected from the group normally consisting of carbon, oxygen, sulfur, nitrogen, and phosphorous, usually carbon and oxygen. The number of heteroatoms in the linking group may range from about 0 to about 8, from about 1 to about 6, or about 2 to about 4. The atoms of the linking group may be substituted with atoms other than hydrogen such as, for example, one or more of carbon, oxygen and nitrogen in the form of, e.g., alkyl, aryl, aralkyl, hydroxyl, alkoxy, aryloxy, or aralkoxy groups. As a general rule, the length of a particular linking group can be selected arbitrarily to provide for convenience of synthesis with the proviso that there is minimal interference caused by the linking group with the ability of the linked molecules to perform their function related to the methods disclosed herein.

The linking group may be aliphatic or aromatic. When heteroatoms are present, oxygen will normally be present as oxy or oxo, bonded to carbon, sulfur, nitrogen or phosphorous; sulfur will be present as thioether or thiono; nitrogen will normally be present as nitro, nitroso or amino, normally bonded to carbon, oxygen, sulfur or phosphorous; phosphorous will be bonded to carbon, sulfur, oxygen or nitrogen, usually as phosphonate and phosphate mono- or diester. Functionalities present in the linking group may include esters, thioesters, amides, thioamides, ethers, ureas, thioureas, guanidines, azo groups, thioethers, carboxylate and so forth. The linking group may also be a macro-molecule such as polysaccharides, peptides, proteins, nucleotides, and dendrimers.

In some embodiments the MS label precursor, or the alteration agent, as the case may be, and the affinity agent may be linked together non-covalently. Members of a binding pair, usually a specific binding pair, are employed where one member is linked to the affinity agent and the other member is linked to the MS label precursor or to the alteration agent. Binding of the binding pair members results in the non-covalent linking of the affinity agent and the MS label precursor or the alteration agent. The binding pair members may be linked directly to one or both of the MS label precursor, or the alteration agent, and the affinity agent or indirectly through the intermediacy of a linking group, the nature of which is discussed above. In some examples, the members of the specific binding pair have a relatively high binding constant such as, by way of illustration and not limitation, avidin (streptavidin)-biotin binding, fluorescein (FITC) and antibody for FITC, rhodamine (Texas red) and antibody for rhodamine, digitonin (DIG) and antibody for DIG, non-human species antibody (e.g., goat, rabbit, mouse, chicken, sheep) and anti-species antibody, for example.

The modified affinity agents can be prepared by linking each different affinity agent in separate, individual reactions to the MS label precursor or the alteration agent and then combining the modified affinity agents to form a mixture comprising the modified affinity agents. Alternatively, the different affinity agents can be combined and the reaction to link the affinity agents to the MS label precursor or the alteration agent can be carried out on the combination. This allows the method to be multiplexed for more than one result at a time.

An amount of each different modified affinity agent that is employed in the methods in accordance with the principles described herein is dependent on one or more of the nature and potential amount of each different population of target rare molecules, the nature of the MS label, the nature of the affinity agent, the nature of a cell if present, the nature of a particle if employed, and the amount and nature of a blocking agent if employed, for example. In some examples, the amount of each different modified affinity agent employed is about 0.001 µg/µL to about 100 µg/µL, or about 0.001 µg/µL to about 80 µg/µL, or about 0.001 µg/µL to about 60 µg/µL, or about 0.001 µg/µL to about 40 µg/µL, or about 0.001 µg/µL to about 20 µg/µL, or about 0.001 µg/µL to about 10 µg/µL, or about 0.5 µg/µL to about 100 µg/µL, or about 0.5 µg/µL to about 80 µg/µL, or about 0.5 µg/µL to about 60 µg/µL, or about 0.5 µg/µL to about 40 µg/µL, or about 0.5 µg/µL to about 20 µg/µL, or about 0.5 µg/µL to about 10 µg/µL, for example.

The number of alteration agents employed may be one per MS label precursor, or one per two MS label precursors, or one per three MS label precursors up to one per all MS label precursors employed depending on one or more of the nature of the MS label precursor, the nature of the alteration agent, whether the alteration agent is free in the medium or part of a modified affinity agent, and the nature and number of different affinity reagents used, for example. For example, where each of the MS label precursors include a labile ester or a labile amide linkage of different MS labels to the affinity agents, a single alteration agent may be employed that results in hydrolysis of the disulfide, ester or amide linkages to yield the different MS labels. In other examples utilizing one alteration agent, or fewer alteration agents than the number of MS label precursors, may be employed. In another example, a different alteration agent can be used to generate an MS label for each different type of affinity agent used.

The combination comprising the concentrated sample and the modified affinity agents in the aqueous medium is treated by holding for a period of time and at a temperature for binding of the modified affinity agents to target rare molecules on the cells or on the particle reagents. For each modified affinity agent that comprises an alteration agent, an MS label precursor upon which the alteration agent acts is included in the combination wherein the MS label precursor is converted to the MS label. In some examples, an additional moiety is added where the alteration agent facilitates the reaction of the moiety with the MS label precursor to yield an MS label. In some examples, the modified affinity agent comprises an MS label precursor and the alteration agent is included in the combination as an unbound substance in the medium. In this example, the alteration agent acts upon the MS label precursor of the affinity agent to produce an MS label. In some examples, a first alteration agent is employed that releases an entity that comprises an MS label precursor from the affinity agent and a second alteration agent is subsequently employed to facilitate the formation of an MS label from an MS label precursor.

The temperature and duration of this treatment is dependent on the nature of the sample, the nature of the target rare molecules, the nature of the non-rare molecules, and the nature of the modified affinity agents, the nature of the MS label precursors, and the nature of the alteration agents, for example. In some examples moderate temperatures are normally employed and usually constant temperature, preferably, room temperature. Temperatures during holding period normally range from about 5° C. to about 99° C. or from about 15° C. to about 70° C., or about 20° C. to about 45° C., for example. The holding period is about 0.2 seconds to about 24 hours, or about 1 second to about 6 hours, or about 2 seconds to about 1 hour, or about 1 to about 15 minutes, for example. The time period depends on, for example, the temperature of the medium and the rate of binding of the various reagents.

Modified affinity agents, i.e., affinity agents that have been acted upon by an alteration agent, which have become bound to target rare molecules are separated from modified affinity agents that have not become bound to target molecules. In some examples, this separation involves reducing the number of non-rare molecules in the sample. In one exemplary approach, a retentate and a filtrate are formed by contacting the treated sample with a porous matrix. Any of a number of filtration techniques may be employed to carry out contact of the sample with a porous matrix. Such filtration techniques include, but are not limited to, microfiltration, ultrafiltration, and cross-flow filtration, for example. In other examples, this separation involves reducing non-rare molecules within the sample by capturing particles with affinity reagents for the rare molecules. The particles can be captured on a surface of the membrane by electrostatic energy, by the binding nature of the membrane, by the chemical nature of the membrane, or by the use of silicate compounds or polymers, for example. In one example, a silicate compound can be employed that increases charge density of, for example, a dendrimer. Additional particles can be separated by contacting the treated sample with a porous matrix employing the same filtration techniques as discussed herein.

The porous matrix is generally part of a filtration module where the porous matrix is part of an assembly for convenient use during filtration. It should be noted that this contact step with a porous matrix may be carried out concomitantly with the aforementioned treatment step, or the contact step with the porous matrix may be carried out subsequent to the aforementioned treatment step.

The porous matrix is a solid or semi-solid material and may be comprised of an organic or inorganic, water insoluble material. The porous matrix can have any of a number of shapes such as, for example, tubular (e.g., hollow fiber, spiral wound, and hollow fine fiber), track-etched, or planar or flat surface (e.g., strip, disk, film, membrane, and plate). The matrix may be fabricated from a wide variety of materials, which may be naturally occurring or synthetic, polymeric or non-polymeric, fibrous or non-fibrous. Examples, by way of illustration and not limitation, of such materials for fabricating a porous matrix include cellulose (including paper), nitrocellulose, cellulose acetate, polycarbonate, poly (vinyl chloride), polyacrylamide, polyacrylate, polyethylene, polypropylene, poly-(4-methylbutene), polystyrene, polymethacrylate, poly(ethylene terephthalate), nylon, and poly(vinyl butyrate), ceramic material, metallic material, for example, either used by themselves or in conjunction with one another and/or with other materials.

In some examples, the size of the pores of a porous matrix is that which is sufficient to preferentially retain certain cells while allowing the passage of other cells through the pores. The size of the pores of the porous matrix is dependent on the nature and size of the different populations of rare cells and non-rare cells, the size of particles employed, and the vacuum applied to the sample on the porous matrix, for example. In some examples the average size of the pores of the porous matrix is about 1 µm to about 100 µm, or about 1 µm to about 75 µm, or about 1 µm to about 50 µm, or about 1 µm to about 20 µm, or about 1 µm to about 10 µm, or about 5 µm to about 100 µm, or about 5 µm to about 75 µm, or about 5 µm to about 50 µm, or about 5 µm to about 20 µm, or about 5 µm to about 10 µm, for example. The density of pores in the porous matrix is about 1% to about 80%, or about 10% to about 80%, or about 20% to about 80%, or about 50% to about 80%, or about 20% to about 70%, for example.

In some examples, vacuum is applied to the concentrated and treated sample on the porous matrix to facilitate passage of non-rare cells through the membrane. The level of vacuum applied is dependent on one or more of the nature and size of the different populations of biological particles, the nature of the porous matrix, and the size of the pores of the porous matrix, for example. In some examples, the level of vacuum applied is about 1 millibar to about 100 millibar, or about 1 millibar to about 80 millibar, or about 1 millibar to about 50 millibar, or about 1 millibar to about 40 millibar, or about 1 millibar to about 30 millibar, or about 1 millibar to about 25 millibar, or about 1 millibar to about 20 millibar, or about 1 millibar to about 15 millibar, or about 1 millibar to about 10 millibar, or about 5 millibar to about 80 millibar, or about 5 millibar to about 50 millibar, or about 5 millibar to about 30 millibar, or about 5 millibar to about 25 millibar, or about 5 millibar to about 20 millibar, or about 5 millibar to about 15 millibar, or about 5 millibar to about 10 millibar, for example. In some examples the vacuum is an oscillating vacuum, which means that the vacuum is applied intermittently at regular of irregular intervals, which may be, for example, about 1 second to about 600 seconds, or about 1 second to about 500 seconds, or about 1 second to about 250 seconds, or about 1 second to about 100 seconds, or about 1 second to about 50 seconds, or about 10 seconds to about 600 seconds, or about 10 seconds to about 500 seconds, or about 10 seconds to about 250 seconds, or about 10 seconds to about 100 seconds, or about 10 seconds to about 50 seconds, or about 100 seconds to about 600 seconds, or about 100 seconds to about 500 seconds, or about 100 seconds to about 250 seconds, for example. In this approach, vacuum is oscillated at about 0 millibar to about 10 millibar, or about 1 millibar to about 10 millibar, or about 1 millibar to about 7.5 millibar, or about 1 millibar to about 5.0 millibar, or about 1 millibar to about 2.5 millibar, for example, during some or all of the application of vacuum to the blood sample. Oscillating vacuum is achieved using an on-off switch, for example, and may be conducted automatically or manually.

Contact of the treated sample with the porous matrix is continued for a period of time sufficient to achieve retention of the target rare cells or the particle-bound target rare molecules on a surface of the porous matrix to obtain a surface of the porous matrix having different populations of target rare cells or the particle-bound target rare molecules as discussed above. The period of time is dependent on one or more of the nature and size of the different populations of target rare cells or particle-bound target rare molecules, the nature of the porous matrix, the size of the pores of the porous matrix, the level of vacuum applied to the blood sample on the porous matrix, the volume to be filtered, and the surface area of the porous matrix, for example. In some examples, the period of contact is about 1 minute to about 1 hour, about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes, for example.

One or both of the retentate and the filtrate are subjected to a second alteration agent that facilitates the formation of an MS label from the MS label precursor from the affinity agent if the first alteration agent does not facilitate the formation of an MS label from the MS label precursor.

One or both of the retentate and the filtrate are subjected to MS analysis to determine the presence and/or amount of each different MS label. The presence and/or amount of each different MS label are related to the present and/or amount of each different population of target rare cells and/or particle-bound target rare molecules.

MS analysis determines the mass-to-charge ratio (m/z) of molecules for accurate identification and measurement. The MS method ionizes of molecules into masses as particles by several techniques that include, but are not limited to, matrix-assisted laser desorption ionization (MALDI), atmospheric pressure chemical ionization (APCI), electrospray ionization (ESI), inductive electrospray ionization (iESI), chemical ionization (CI), and electron ionization (EI), fast atom bombardment (FAB), field desorption/field ionization (FC/FI), thermospray ionization (TSP), nanospray ionization, for example. The masses are filtered and separated in the mass detector by several techniques that include, by way of illustration and not limitation, Time-of-Flight (TOF), ion traps, quadrupole mass filters, sector mass analysis, multiple reaction monitoring (MRM), and Fourier transform ion cyclotron resonance (FTICR), for example. The MS method detects the molecules using, for example, a microchannel plate, electron multiplier, or Faraday cup. The MS method can be repeated as a tandem MS/MS method, in which charged mass particles from a first MS are separated into a second MS. Pre-processing steps for separating molecules of interest, such as, by way of example, ambient ionization, liquid chromatography (LC), gas chromatography (GC), and affinity separation, can be used prior to the MS method.

Mass analyzers include, but are not limited to, quadrupoles, time-of-flight (TOF) analyzers, magnetic sectors, Fourier transform ion traps, and quadrupole ion traps, for example. Tandem (MS-MS) mass spectrometers are instruments that have more than one analyzer. Tandem mass spectrometers include, but are not limited to, quadrupole-quadrupole, magnetic sector-quadrupole, quadrupole-time-of-flight, for example. The detector of the mass spectrometer may be, by way of illustration and not limitation, a photo-multiplier, an electron multiplier, or a micro-channel plate, for example.

Following the analysis by mass spectrometry, the presence and/or amount of each different mass spectrometry label is related to the present and/or amount of each different population of target rare cells and/or the particle-bound target rare molecules. The relationship between the MS label and a target molecule is established by the modified affinity agent employed, which is specific for the target molecule. Calibrators are employed to establish a relationship between an amount of signal from an MS label and an amount of target rare molecules in the sample.

An example of a method in accordance with the principles described herein is depicted in FIG. 1. Sample is collected into a container with a suitable cell buffer. The collected sample is subjected to filtration to concentrate the number of cell-bound target rare molecules over that of other molecules in the sample such as, for example, non-rare cells. An affinity agent that comprises an alteration agent linked to an antibody that is specific for the cell-bound target rare molecule is combined with the concentrated sample retained on a membrane of a filtration device. After a suitable incubation period, the membrane is washed with a buffer. An MS label precursor is added to the sample on the membrane. The alteration agent of the affinity agent is part of an immune complex comprising the affinity agent and the cell-bound target molecule. If the target rare molecule is present in the sample, the alteration agent acts upon the MS label precursor to produce an MS label that corresponds to the target rare molecule. The reacted sample is collected by, for example, pipette, from the membrane of the filtration device and is subjected to MS analysis. If the target rare molecule is present in the sample, the MS label will give a distinctive spectrum that corresponds to the target rare molecule. In the example of FIG. 1, detection of only one target rare molecule is depicted; however, it is to be appreciated that any number of target rare molecules may be determined in a single method on a single sample using various MS label precursors as discussed above as discussed above in accordance with the principles described herein.

Figure 2:
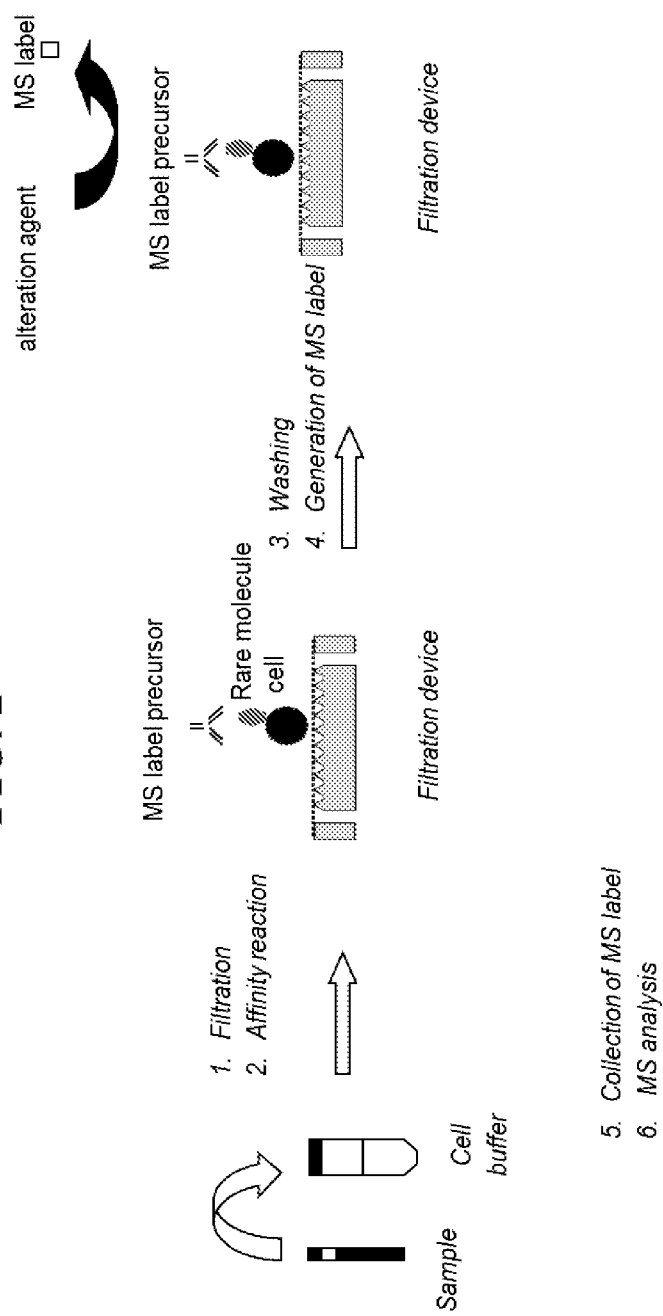
FIG. 2 is a schematic depicting an example of a method in accordance with the principles described herein for a target molecule that is associated with a cell and the alteration agent is not attached to the affinity agent

Another example of a method in accordance with the principles described herein is depicted in FIG. 2. Sample is collected into a container with a suitable cell buffer. The collected sample is subjected to filtration to concentrate the number of cell-bound target rare molecules over that of other molecules in the sample such as, for example, non-rare cells. An affinity agent that comprises an MS label precursor linked to an antibody that is specific for the cell-bound target rare molecule is combined with the concentrated sample retained on a membrane of a filtration device. After a suitable incubation period, the membrane is washed with a buffer. An alteration agent is added to the sample on the membrane. The MS label precursor of the affinity agent is part of an immune complex comprising the affinity agent and the cell-bound target molecule. If the target rare molecule is present in the sample, the alteration agent acts upon the MS label precursor to produce an MS label that corresponds to the target rare molecule. The reacted sample is collected by, for example, pipette, from the membrane of the filtration device and is subjected to MS analysis. If the target rare molecule is present in the sample, the MS label will give a distinctive spectrum that corresponds to the target rare molecule. In the example of FIG. 2, detection of only one target rare molecule is depicted; however, it is to be appreciated that any number of target rare molecules may be determined in a single method on a single sample using various MS label precursors as discussed above as discussed above in accordance with the principles described herein.

Figure 3:
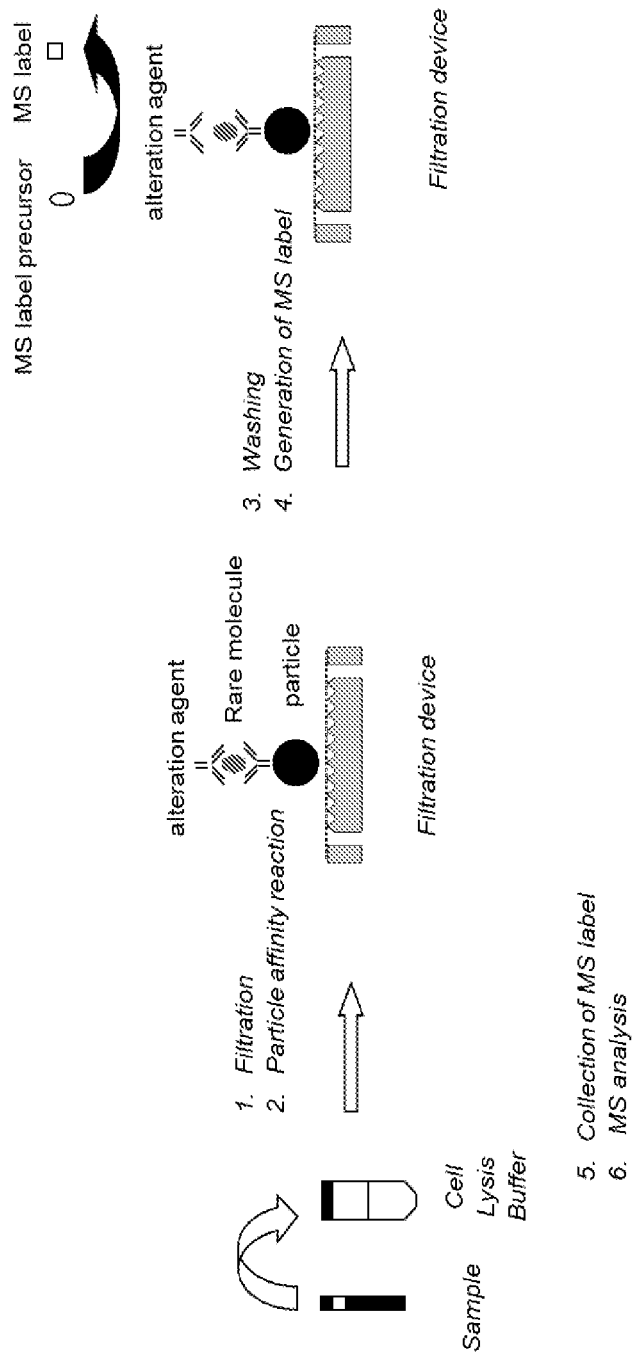
FIG. 3 is a schematic depicting an example of a method in accordance with the principles described herein for a target molecule that is not associated with a cell and the alteration agent is attached to the affinity agent.

Another example of a method in accordance with the principles described herein is depicted in FIG. 3. Sample is collected into a container with a suitable cell buffer. In this example, the target rare molecule is non-particulate, i.e., the target rare molecule is not bound to a cell or other particle. The collected sample is combined with a particle reagent that comprises a particle to which is attached an antibody for the target rare molecule. After an incubation period to permit binding of the non-cell-bound target rare molecule to the antibody on the particle to give particle-bound non-cell-bound target rare molecule, the sample is subjected to filtration to concentrate the number of particle-bound non-cell-bound target rare molecules over that of other molecules in the sample such as, for example, non-rare cells. Sample retained on the surface of the filtration device is washed with a suitable buffer. An affinity agent that comprises an alteration agent linked to an antibody that is specific for the particle-bound non-cell-bound target rare molecule is combined with the concentrated sample retained on a membrane of a filtration device. After a suitable incubation period, the membrane is washed with a buffer. An MS label precursor is added to the sample on the membrane. The alteration agent of the affinity agent is part of an immune complex comprising the affinity agent and the particle-bound non-cell-bound target molecule. If the target rare molecule is present in the sample, the alteration agent acts upon the MS label precursor to produce an MS label that corresponds to the target rare molecule. The reacted sample is collected by, for example, pipette, from the membrane of the filtration device and is subjected to MS analysis. If the target rare molecule is present in the sample, the MS label will give a distinctive spectrum that corresponds to the target rare molecule. In the example of FIG. 3, detection of only one non-cell-bound target rare molecule is depicted; however, it is to be appreciated that any number of target rare molecules (both cell-bound and non-cell bound) may be determined in a single method on a single sample using various MS label precursors as discussed above in accordance with the principles described herein.

Figure 4:
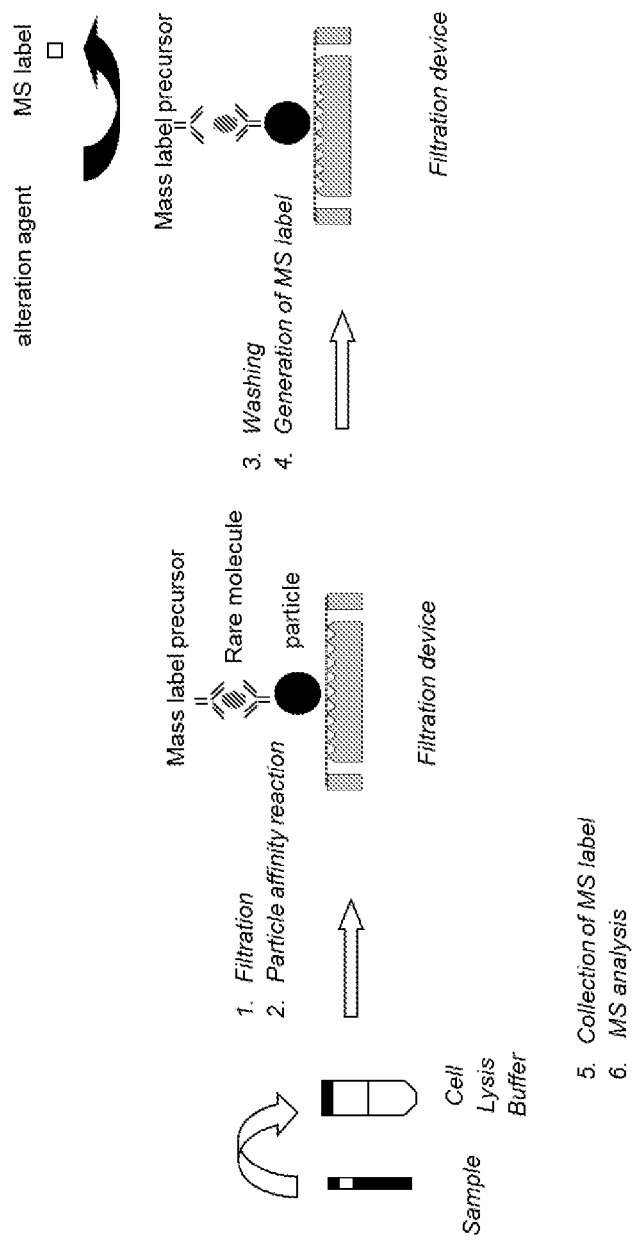
FIG. 4 is a schematic depicting an example of a method in accordance with the principles described herein for a target molecule that is not associated with a cell and the alteration agent is not attached to the affinity agent.

Another example of a method in accordance with the principles described herein is depicted in FIG. 4. Sample is collected into a container with a suitable cell buffer. In this example, the target rare molecule is non-particulate, i.e., the target rare molecule is not bound to a cell or other particle. The collected sample is combined with a particle reagent that comprises a particle to which is attached an antibody for the target rare molecule. After an incubation period to permit binding of the non-cell-bound target rare molecule to the antibody on the particle to give particle-bound non-cell-bound target rare molecule, the sample is subjected to filtration to concentrate the number of particle-bound non-cell-bound target rare molecules over that of other molecules in the sample such as, for example, non-rare cells. Sample retained on the surface of the filtration device is washed with a suitable buffer. An affinity agent that comprises an MS label precursor linked to an antibody that is specific for the particle-bound non-cell-bound target rare molecule is combined with the concentrated sample retained on a membrane of a filtration device. After a suitable incubation period, the membrane is washed with a buffer. An alteration agent is added to the sample on the membrane. The MS label precursor of the affinity agent is part of an immune complex comprising the affinity agent and the particle-bound non-cell-bound target molecule. If the target rare molecule is present in the sample, the alteration agent acts upon the MS label precursor to produce an MS label that corresponds to the target rare molecule. The reacted sample is collected by, for example, pipette, from the membrane of the filtration device and is subjected to MS analysis. If the target rare molecule is present in the sample, the MS label will give a distinctive spectrum that corresponds to the target rare molecule. In the example of FIG. 4, detection of only one non-cell-bound target rare molecule is depicted; however, it is to be appreciated that any number of target rare molecules (both cell-bound and non-cell bound) may be determined in a single method on a single sample using various MS label precursors as discussed above in accordance with the principles described herein.

Figure 5:
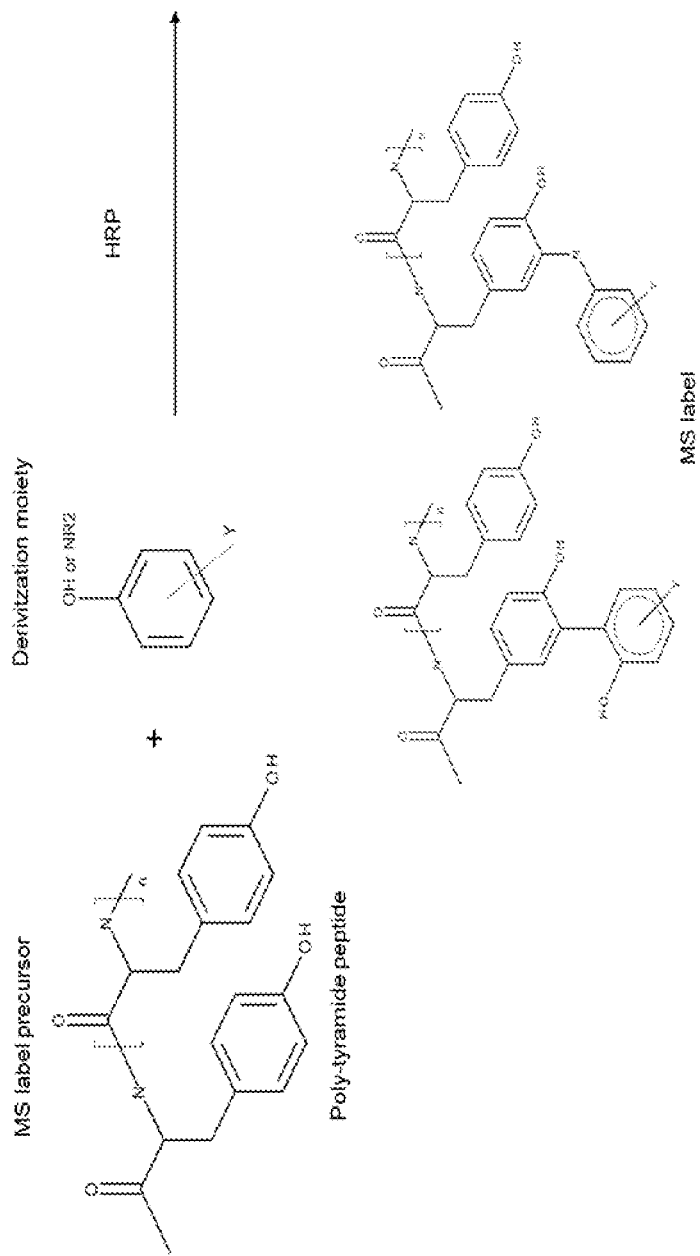
FIG. 5 is a depiction of an example of the generation of an MS label from an MS label precursor in a method according to an example in accordance with the principles described herein where the MS label precursor is altered to add a derivitization moiety where an MS label is formed.

FIG. 5 depicts an example of an MS label precursor (poly-tyramide peptide) that forms an MS label by addition of a phenol or an aromatic amine ($NR^2$ wherein R is alkyl) to the MS label precursor in the presence of an alteration agent (the enzyme HRP in this example). Multiplexing can be achieved in this example by, for example, variation of the poly-tyramide peptide (by number (n) of groups within the bracket so that a distinctive poly-tyramide peptide can be used as an MS label precursor for each of the different target rare molecules that are to be determined in a sample.

Figure 6:
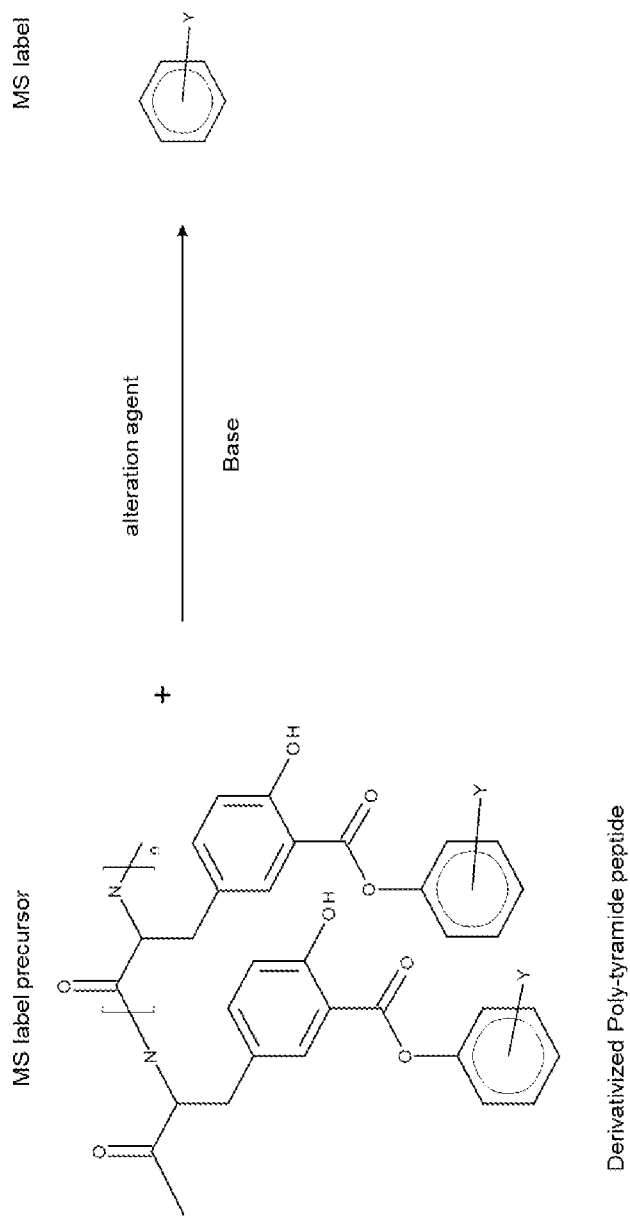
FIG. 6 is a depiction of an example of the generation of an MS label from an MS label precursor in a method according to an example in accordance with the principles described herein where the MS label precursor is altered to release many MS labels.

FIG. 6 depicts an example of the generation of an MS label from an MS label precursor (derivatized poly-tyramide peptide) in a method in accordance with the principles described herein where the MS label precursor is altered by the alteration agent (in this example, a base that cleaves the ester bond attaching the Y-substituted phenyl group to the peptide) to release many MS labels.

Examples of Methods in Accordance with the Principles Described Herein Employing Particle Amplification As mentioned above, in one approach, particle amplification is utilized and provides for the aggregation or clustering particles to form particle aggregates that comprise MS labels or MS label precursors.

The phrase "particle amplification" refers to the formation of aggregates or clusters of particles wherein a number of label particles indicative of a single target rare molecule is enhanced. In some examples, the number of label molecules in a particle aggregate that is indicative of a target rare molecule is $10^{10}$ to 1, or $10^9$ to 1, or $10^8$ to 1, or $10^7$ to 1, or $10^6$ to 1, or $10^5$ to 1, or $10^4$ to 1, or $10^3$ to 1, or $10^2$ to 1, or 10 to 1, or $10^{10}$ to $10^2$, or $10^{10}$ to $10^3$, or $10^{10}$ to $10^4$, or $10^{10}$ to $10^5$, for example. Particle amplification is achieved by employing a larger particle (carrier particle) associated with many smaller label particles that have many MS label or MS label precursors associated therewith.

The term "associated with" refers to the manner in which two moieties are bound to one another. The association may be through covalent or non-covalent binding as defined above. The attachment may be accomplished by a direct bond between the two moieties or a linking group can be employed between the two moieties. Linking groups may be, for example, as described above.

The composition of the carrier particle may be, for example, as described above for capture particle entities. The size of the carrier particle is large enough to accommodate one or more label particles. The ratio of label particles to a single carrier particle may be $10^6$ to 1, or $10^5$ to 1, or $10^4$ to 1, or $10^3$ to 1, or $10^2$ to 1, or 10 to 1, for example. The diameter of the carrier particle is also dependent on one or more of the nature of the target rare molecule, the nature of the sample, the nature and the pore size of a filtration matrix, the adhesion of the particle to matrix, the surface of the particle, the surface of the matrix, the liquid ionic strength, liquid surface tension and components in the liquid, and the number, size, shape and molecular structure of associated label particles, for example. When a porous matrix is employed in filtration separation step, the diameter of the carrier particles must be large enough to hold a number of label particles to achieve the benefits of particle amplification in accordance with the principles described herein but small enough to be pass through the pores of a porous matrix or membrane of a filtration device in accordance with the principles described herein. In some examples in accordance with the principles described herein, the average diameter of the carrier particles should be at least about 0.1 microns and not more than about 1 micron, or not more than about 5 microns. In some examples, the carrier particles have an average diameter from about 0.1 microns to about 5 microns, or about 1 micron to about 3 microns, or about 4 microns to about 5 microns, about 0.2 microns to about 0.5 microns, or about 1 micron to about 3 microns, or about 4 microns to about 5 microns, for example.

The composition of the label particle may be, for example, as described above for capture particle entities. The size of the label particles is dependent on one or more of the nature and size of the carrier particle, the nature and size of the MS label, or the MS label precursor, of the alteration agent, the nature of the target rare molecule, the nature of the sample, the nature and the pore size of a filtration matrix, the surface of the particle, the surface of the matrix, the liquid ionic strength and, liquid surface tension and components in the liquid, for example. In some examples in accordance with the principles described herein, the average diameter of the label particles should be at least about 0.01 microns and not more than about 0.1 microns, or not more than about 1 micron. In some examples, the label particles have an average diameter from about 0.01 microns to about 1 micron, or about 0.01 microns to about 0.5 microns, or about 0.01 microns to about 0.4 microns, or about 0.01 microns to about 0.3 microns, or about 0.01 microns to about 0.2 microns, or about 0.01 microns to about 0.1 microns, or about 0.01 microns to about 0.05 microns, or about 0.1 microns to about 0.5 microns, or about 0.05 microns to about 0.1 microns, for example. In some examples, the label particle may be a silica nanoparticle, which can be linked to magnetic carrier particles that have free carboxylic acid groups by ionic association.

The number of MS labels or MS label precursors associated with the label particle is dependent on one or more of the nature and size of the MS label or MS label precursor, the nature and size of the label particle, the nature of the linker arm, the number and type of functional groups on the label particle, and the number and type of functional groups on the MS label precursor, for example. In some examples, the number of MS labels or MS label precursors associated with a single label particle is about $10^7$ to 1, or about $10^6$ to 1, or about $10^5$ to 1, or about $10^4$ to 1, or about $10^3$ to 1, or about $10^2$ to 1, or about 10 to 1, for example.

As mentioned above, some examples in accordance with the principles described herein are directed to methods of one or more different populations of target rare molecules in a sample suspected of containing the one or more different populations of rare molecules and non-rare molecules. The sample that has an enhanced concentration of the one or more different populations of target rare molecules over that of the non-rare molecules wherein the target rare molecules are in particulate form is incubated with, for each different population of target rare molecules, an affinity agent that comprises a specific binding partner that is specific for and binds to a target rare molecule of one of the populations of the target rare molecules. The affinity agent comprises an MS label precursor or a first alteration agent. For each different population of target rare molecules, the affinity agent comprises a particle reagent. The first alteration agent facilitates the formation of an MS label from the MS label precursor or releases an entity that comprises the MS label precursor from the affinity agent. During the incubating, for each different population of target rare molecules, particle aggregates are formed from the particle reagent of the affinity agent. A retentate and a filtrate are formed by contacting the incubated samples with a porous matrix. One or both of the retentate and the filtrate are subjected to a second alteration agent that facilitates the formation of an MS label from the MS label precursor from the affinity agent for each different population of target rare molecules when the first alteration agent does not facilitate the formation of an MS label from the MS label precursor. One or both of the retentate and the filtrate are subjected to MS analysis to determine the presence and/or amount of each different MS label, and the presence and/or amount of each different MS label is related to the present and/or amount of each different population of non-cellular target rare molecules in the sample.

The size of the particle aggregates is dependent on one or more of the nature and size of the capture particle, the nature and size of the carrier particle, the nature and size of the label particle, the nature and size of the linking groups, the nature and size of the MS label or the MS label precursor, the nature of the alteration agent, the nature of the target rare molecule, the nature of the sample, the nature and the pore size of a filtration matrix, the surface of the particle, the surface of the matrix, the liquid ionic strength and, liquid surface tension and components in the liquid, for example. In some examples in accordance with the principles described herein, the average diameter of the particle aggregates is at least about 0.1 microns and not more than about 500 microns, or not more than about 1,000 microns. In some examples, the particle aggregates have an average diameter from about 0.1 microns to about 1,000 microns, or about 0.1 microns to about 500 microns, or about 0.1 microns to about 100 microns, or about 0.1 microns to about 10 microns, or about 0.1 microns to about 5 microns, or about 0.1 microns to about 1 micron, or about 1 micron to about 10 microns, or about 10 microns to about 500 microns, or about 10 microns to about 100 microns, for example.

Figure 7:
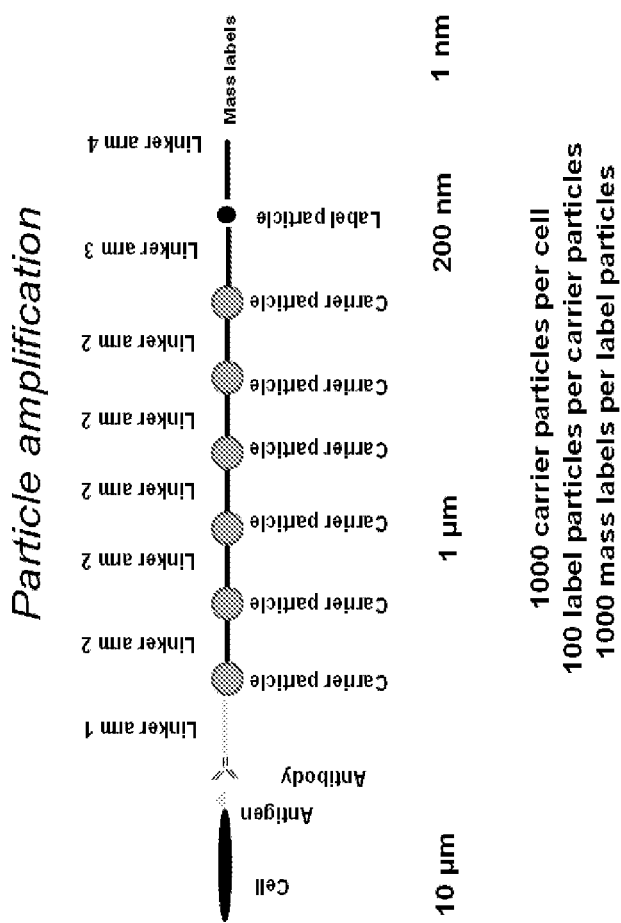
FIG. 7 is a depiction of an example of particle amplification according to an example in accordance with the principles described herein.

One example of a particle amplification approach to methods in accordance with the principles described herein may be seen with reference to FIG. 7. In the example of FIG. 7, the target rare molecule (Antigen) is attached to the surface of a cell on the order of about 10 microns (μm). Carrier particles having an average diameter of about 1 μm in this example are linked by means of a first linking group (Linker arm 1) to a specific binding partner (Antibody) for the Antigen. A second linking group (Linker arm 2) links additional Carrier particles to one another in a linear manner. In this example, the number of Carrier particles per cell is about 1,000. Furthermore, there are approximately 100 Label particles (about 200 nm in diameter) per each Carrier particle linked thereto by means of a third linking group (Linker arm 3). For each Label particle there are about $10^5$ MS labels (Mass labels) linked thereto by means of a fourth linking group (Linker arm 4). In this example, the MS labels have a size of about 1 nm. Linker arms 1-4 may be chosen from any linking group as described above and two or more thereof may be the same or each of the Linker arms may be different from one another. In some examples, one or more of Linker arms 1-4 have a cleavable moiety so that, for example, Carrier particles may be cleaved from one another or from the cell and/or Label particles may be cleaved from the Carrier particles, and/or MS labels or MS label precursors may be cleaved from the Label particles. Cleavage of the various Linker arms may be carried out sequentially where the cleavable moieties of the Linker arms differ from one another.

As mentioned above, one or more linking groups may comprise a cleavable moiety that is cleavable by a cleavage agent. The nature of the cleavage agent is dependent on the nature of the cleavable moiety. Cleavage of the cleavable moiety may be achieved by chemical or physical methods, involving one or more of oxidation, reduction, solvolysis, e.g., hydrolysis, photolysis, thermolysis, electrolysis, sonication, and chemical substitution, for example. Examples of cleavable moieties and corresponding cleavage agents, by way of illustration and not limitation, include disulfide that may be cleaved using a reducing agent, e.g., a thiol; diols that may be cleaved using an oxidation agent, e.g., periodate; diketones that may be cleaved by permanganate or osmium tetroxide; diazo linkages or oxime linkages that may be cleaved with hydrosulfite; O-sulfones, which may be cleaved under basic conditions; tetralkylammonium, trialkylsulfonium, tetralkylphosphonium, where the α-carbon is activated, e.g., with carbonyl or nitro, that may be cleaved with base; ester and thioester linkages that may be cleaved using a hydrolysis agent such as, e.g., hydroxylamine, ammonia or trialkylamine (e.g., trimethylamine or triethylamine) under alkaline conditions; quinones where elimination occurs with reduction; substituted benzyl ethers that can be cleaved photolytically; carbonates that can be cleaved thermally; metal chelates where the ligands can be displaced with a higher affinity ligand; thioethers that may be cleaved with singlet oxygen; hydrazone linkages that are cleavable under acidic conditions; quaternary ammonium salts (cleavable by, e.g., aqueous sodium hydroxide); trifluoroacetic acid-cleavable moieties such as, e.g., benzyl alcohol derivatives, teicoplanin aglycone, acetals and thioacetals; thioethers that may be cleaved using, e.g., HF or cresol; sulfonyls (cleavable by, e.g., trifluoromethane sulfonic acid, trifluoroacetic acid, or thioanisole); nucleophile-cleavable sites such as phthalamide (cleavable, e.g., with substituted hydrazines); ionic association (attraction of oppositely charged moieties) where cleavage may be realized by changing the ionic strength of the medium, adding a disruptive ionic substance, lowering or raising the pH, adding a surfactant, sonication, and adding charged chemicals; and photocleavable bonds that are cleavable with light having an appropriate wavelength such as, e.g., UV light at 300 nm or greater; for example.

Figure 8:
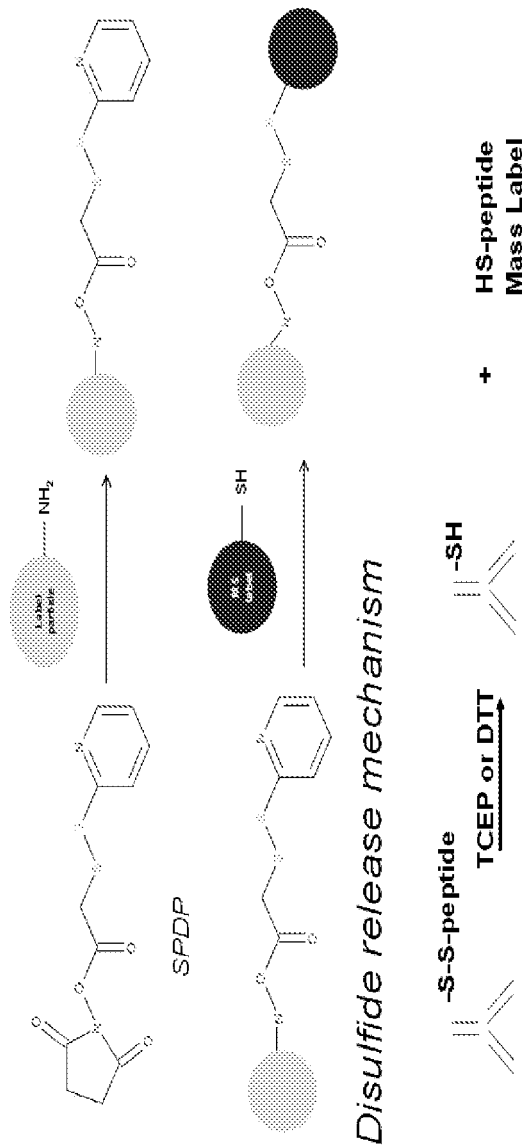
FIG. 8 is a depiction of an example of an MS label precursor prepared by SPDP conjugation according to an example in accordance with the principles described herein.

In one example in accordance with the principles described herein, a cleavable linkage may be formed using conjugation with N-succinimidyl 3-(2-pyridyldithio)propionate) (SPDP), which comprises a disulfide bond. For example (see FIG. 8), a label particle comprising an amine functionality is conjugated to SPDP and the resulting conjugate can then be reacted with a MS label comprising a thiol functionality, which results in the linkage of the MS label moiety to the conjugate. A disulfide reducing agent (such as, for example, dithiothreitol (DTT) or tris(2-carboxyethyl) phosphine (TCEP)) may be employed as an alteration agent to release a thiolated peptide as an MS label.

Figure 9:
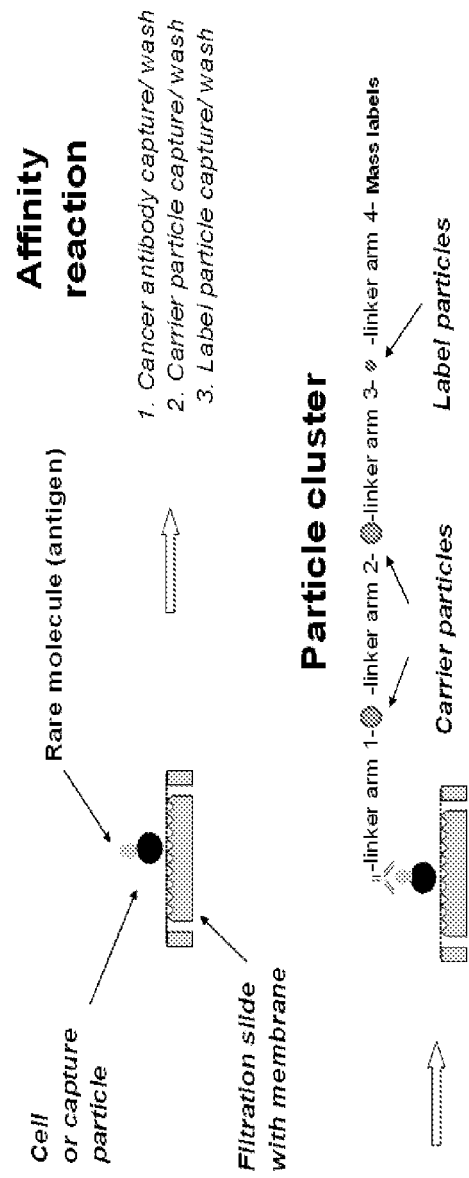
FIG. 9 is a depiction of an example of formation of a particle cluster on a membrane according to an example in accordance with the principles described herein.

FIG. 9 depicts an example, by way of illustration and not limitation, of the formation of a particle aggregate (particle cluster) on a membrane of a filtration device. Referring to FIG. 9, a cell or a capture particle that has captured a non-particulate target rare molecule in a sample is contacted with a membrane of a filtration slide, wherein the size of the pores of the membrane are as described above for retaining cells or particle-bound target rare molecules. After suitable washing to remove non-particulate material and to reduce the number of non-rare molecules and non-rare cells as discussed above, a set of carrier particles as described above is added for each different population of target rare molecules where each set of the carrier particles comprise a specific binding partner specific for a different target rare molecule to be determined. The specific binding partner is linked to the carrier particle by means of a first linking group (Linker arm 1). Carrier particles are linked to one another employing a second linking group (Linker arm 2). After another washing step, label particles are added where each set of the label particles comprise an MS label or an MS label precursor for a different target rare molecule to be determined. The label particles comprise a functionality that is reactive with a functionality on the carrier particles. The reaction of the functionalities provides for the formation of a third linking group (Linker arm 3). The MS labels or the MS label precursors are bound to the label particles by means of a fourth linking group (Linker arm 4). The resultant entity may be similar to that depicted in FIG. 7 for each different target rare molecule. As a result, a particle cluster is formed comprising the target rare molecule, the carrier particles, the label particles and the MS labels or MS label precursors.

Particle aggregates that are retained on the surface of a membrane of a filtration device in accordance with the principles described herein may be removed by any convenient method. Examples of such methods include, but are not limited to, punching out the particle aggregate from the membrane into a suitable vessel, extraction of the particle aggregate from the membrane, filtering the carrier particles with label particles through the membrane, or by picking up carrier particles with label particles from the membrane, for example.

In the punch out approach, the membrane is cut into areas containing the cell or capture particle using an implement to segment or cut out the area. Such implements include, but are not limited to, a punch, a laser, and a cutting edge, for example. The area can be selected based on the presence of pores or by being pre-scribed for break-away. The area falls or is gathered into a well for treatment with liquids for washing and release of MS labels or MS label precursors. Alternatively, the particle can be held by a magnetic force at the bottom of the well so they do not interfere with analysis. In the punch out approach, only linker arm 4 needs to be cleavable to release the MS label or MS label precursor into solution for analysis.

In the extraction of the particle aggregate approach, the membrane area is partially or completely washed with a liquid to remove the particles. Linker arm 1 can be cleavable for the particles to be removed without damage to the rare cell or target rare molecule. Alternatively, sonication of the membrane into a liquid can aid the extraction and break the particles from the rare cell or target rare molecule without a cleavable linker arm 1. The area extracted can be selected based on the presence of a cell or capture particle. The extracted particles can be gathered by centrifuging and then treated with liquids for washing and release of the MS label or MS label precursor. In another alternative, the particle can be gathered and held by a magnetic force. Linker arm 4 should be cleavable to release the MS label or MS label precursor into solution for analysis.

The filtration approach is described above; the average size of the pores of the filtration membrane is that which will permit the carrier particles with label particles to pass through the membrane while retaining particle aggregates on the surface of the membrane. The membrane area is partially or completely washed with a liquid to remove the particles. Linker arm 1 should be cleavable for the particles to be removed. In addition, the association between carrier particles in linker arm 2 should be cleavable if the combined carrier particle size exceeds the average size of the pores of the filtration membrane. The extracted liquids and particles are gathered by centrifuging and treated with additional liquids for washing and release of the MS label or MS label precursor. Furthermore, the particle can be gathered and held by a magnetic force. Linker arm 4 should be cleavable to release the MS label or MS label precursor into solution for analysis.

Figure 13:
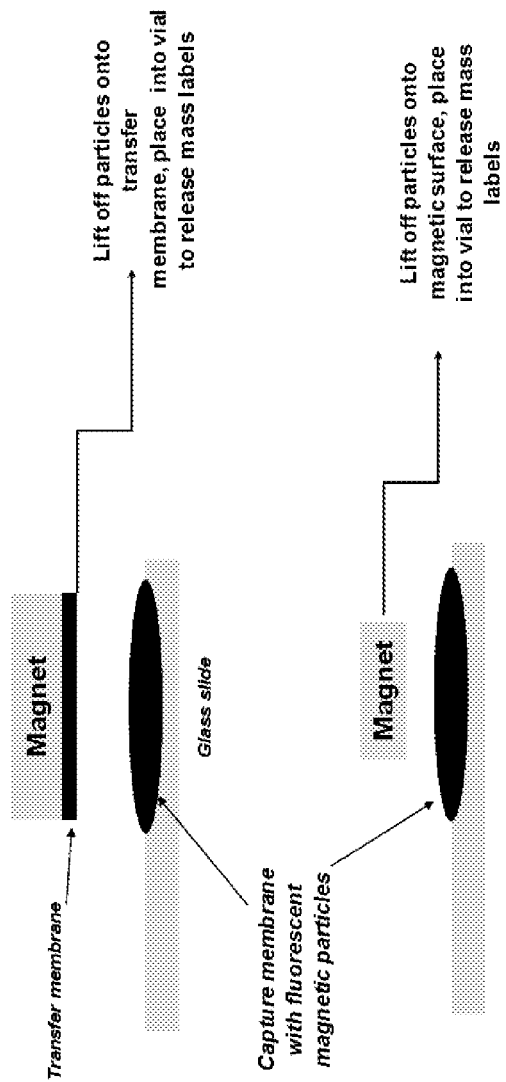
FIG. 13 is a depiction of an example the use of transfer surfaces and magnetic force for particle removal from a membrane according to an example in accordance with the principles described herein.

In the pickup aspect of the particle aggregate approach, the membrane area is partially or completely contacted with a surface capable of removing the particles. Linker arm 1 should be cleavable for the particles to be removed without breaking or damaging the rare cell or the target rare molecule. The area extracted can be selected based on the presence of a cell or a capture particle. The extracted particles can be gathered on the removal surface and treated with liquids for washing and release of the MS label or MS label precursor. In addition or alternatively, the particle can be gathered and held by a magnetic force. Linker arm 4 should be cleavable to release the MS label or MS label precursor into solution for analysis. A magnet itself may be employed as the surface or a magnet may be employed in conjunction with a transfer surface to assist in carrier particle removal from a membrane when the carrier particles are magnetic. After the magnetic carrier particle is affinity captured to a cell or a capture particle on the membrane, the carrier particle must be removed for MS analysis. FIG. 13 depicts two examples of the use of magnetic force for carrier particle pick up by way of illustration and not limitation. In one approach, an unprotected magnet is employed and in another approach a magnet is employed that is protected by a transfer surface. A second membrane is used as a transfer surface or transfer membrane. The motility of the magnetic particles is tested by application of a magnetic force to a glass slide (shown on bottom of FIG. 13) after the magnetic particles are added to a carrier membrane or directly to a glass slide In some examples, one or more of the linking groups are formed covalently as described above employing appropriate corresponding functionalities of functional groups as discussed above. In some examples, one of more of the linking groups is formed non-covalently as discussed above. Members of a binding pair, usually a specific binding pair, are employed where one member is linked to one linking group moiety and the other member is linked to a second linking group moiety. When the binding pair members bind, the linking group is formed that includes the binding pair members and the two linking group moieties. Binding of the binding pair members results in the non-covalent linking of the two linking group moieties that ultimately form the linking group. The linking group moieties may be a bond or a linking group as discussed above. As mentioned above, the members of the binding pair have a relatively high binding constant such as, by way of illustration and not limitation, avidin (streptavidin)-biotin binding, fluorescein (FITC) and antibody for FITC, rhodamine (Texas red) and antibody for rhodamine, digitonin (DIG) and antibody for DIG non-human species antibody (e.g., goat, rabbit, mouse, chicken, sheep) and anti-species antibody, for example.

Figure 10:
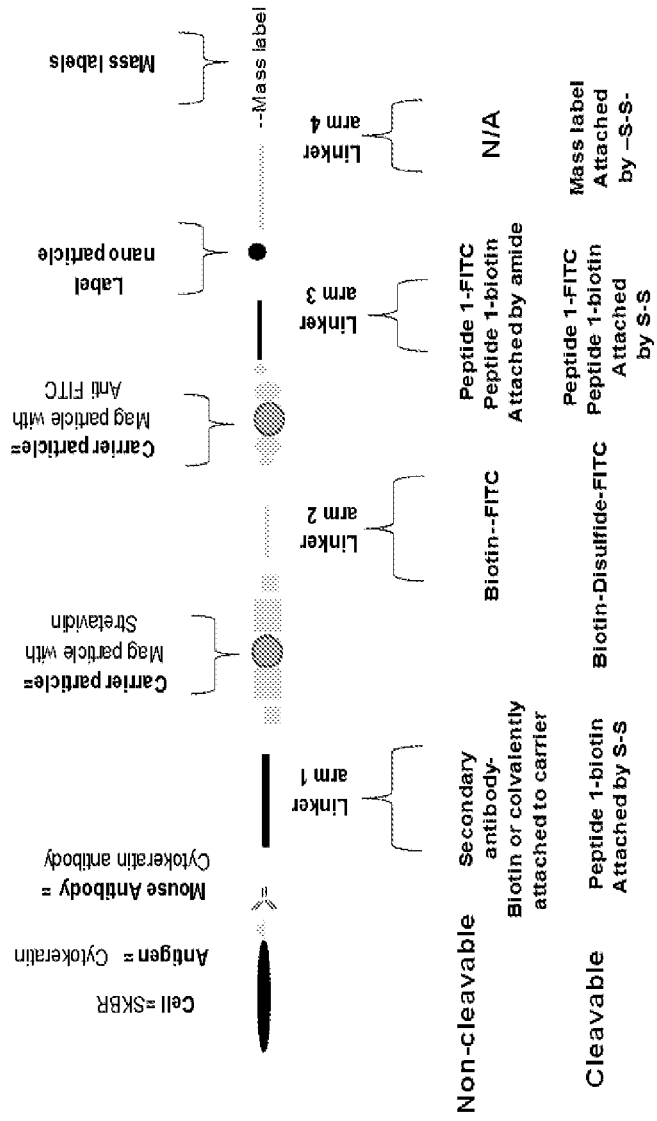
FIG. 10 is a depiction of an example of various changes that may be made to linker arms employed in examples of conjugates according to an example in accordance with the principles described herein.

Referring to FIG. 10, in some examples, by way of illustration and not limitation, Linker arm 1 may involve a non-cleavable bond employing a secondary antibody linked to biotin where the secondary antibody binds to the antibody for the target rare molecule and the biotin binds to streptavidin molecules on the surface of a Carrier particle. Alternatively, the antibody can be directly conjugated to the Carrier particle through amide bounds to the carboxylic acids on the particle and amines on the antibody using commonly known bioconjugation methods. In another example, Linker arm 1 may involve a cleavable linkage employing a small molecule peptide such as, e.g., Peptide 1, linked to biotin and attached to the antibody by a disulfide linker made by reaction with, for example, SPDP. In some examples, Linker arm 2 may include a non-cleavable linkage where the Carrier particle has streptavidin molecules on its surface and a conjugate of biotin and a small molecule such as, for example, biotin-FITC, is employed to form the linking group. When a cleavable linkage is desired for Linker arm 2, the biotin-FITC agent includes a cleavable moiety such as, for example, a disulfide bond. The small molecule portion, e.g., FITC portion, of Linker arm 2 binds to a binding partner for the small molecule (e.g., an antibody for FITC) on the surface of the Carrier particle. Linker arm 3 may include a non-cleavable linkage where the linking moiety has Peptide 1 attached to FITC or biotin by an amide bond or Linker arm 3 may include a cleavable linkage where the linking moiety has Peptide 1 attached to FITC or biotin by a disulfide bond. Linker arm 3 may include an ionic linkage where the ionized amines or other groups on the label particle are attracted to the ionized carboxylic acid or other groups on the label particle. As explained above, an MS label or MS label precursor is attached to a label particle by a cleavable bond such as, but not limited to, a peptide or other MS label attached by a disulfide bond.

The phrase "small molecule" refers to a molecule having a molecular weight in the range of about 100 to about 2,000, or about 200 to about 2,000, or about 300 to about 2,000, or about 500 to about 2,000, or about 1,000 to about 2,000, or about 500 to about 1,500, or about 1,000 to about 1,500, or about 1,000 to about 1,200, for example. Examples of small molecules, by way of illustration and not limitation, include biotin, digoxin, digoxigenin, 2,4-dinitrophenyl, fluorescein, rhodamine, small peptides (meeting the aforementioned molecular weight limits), vitamin B12 and folate, for example. Examples of small molecule-binding partner for the small molecule pairs, by way of illustration and not limitation, include biotin-binding partner for biotin (e.g., avidin, streptavidin and antibody for biotin), digoxin-binding partner for digoxin (e.g., antibody for digoxin), digoxigenin-binding partner for digoxigenin (e.g., antibody for digoxigenin), 2,4-dinitrophenyl and binding partner for 2,4-dinitrophenyl (e.g., antibody for 2,4-dinitrophenyl), fluorescein-binding partner for fluorescein (e.g., antibody for fluorescein), rhodamine-binding partner for rhodamine (e.g., antibody for rhodamine), peptide-binding partner for the peptide (e.g., antibody for the peptide), analyte-specific binding partners (e.g., intrinsic factor for B12, folate binding factor for folate), for example.

Examples of small molecule peptides, which may function also as MS labels, include, by way of illustration and not limitation, peptides that comprise two or more of histidine, lysine, phenylalanine, leucine, alanine, methionine, asparagine, glutamine, aspartic acid, glutamic acid, tryptophan, proline, valine, tyrosine, glycine, threonine, serine, arginine, cysteine and isoleucine and derivatives thereof. In some examples, the peptides have a molecular weight of about 100 to about 3,000 mass units and may contain 3 to 30 amino acids. In some examples, the peptides comprise nine amino acids selected from the group consisting of tyrosine, glycine, methionine, threonine, serine, arginine, phenylalanine, cysteine and isoleucine and have masses of 1,021.2; 1,031.2; 1,033.2; 1,077.3; 1,087.3; 1,127.3; 1,137 mass units; or 3 amino acids from the above group and having masses of 335.4, 433.3, 390.5, 426.5, and 405.5 mass units. The number of amino acids in the peptide is determined by, for example, the nature of the MS technique employed. For example, when using MALDI for detection, the peptide can have a mass in the range of about 600 to about 3,000 mass units and is constructed of about 6 to about 30 amino acids. Alternatively, when using EIS for detection, the peptide has a mass in the range of about 100 to about 1,000 and is constructed of 1 to 9 amino acids or derivatives of, for example. In some examples, the number of amino acids in the peptide label may be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, for example.

The use of peptides as MS labels has several advantages, which include, but are not limited to, the following: 1) relative ease of conjugation to proteins, antibodies, particles and other biochemical entities; 2) relative ease with which the mass can be altered to allow many different masses thus providing for multiplexed assay formats and standards; and 3) adjustability of the mass to a mass spectrometer used. For conjugation, the peptides can have a terminal cysteine that is employed in the conjugation. For ionization, the peptides can have charged amine groups. In some examples, the amino acid peptides have N-terminal free amine and C-terminal free acid. In some examples, the amino acid peptides are isotope labeled or derivatized with an isotope. The peptides may be conjugated to a small molecule such as, for example, biotin or fluorescein, for binding to a corresponding binding partner for the small molecule, which in this example is streptavidin or antibody for fluorescein. Biotin or fluorescein may be conjugated at the N-terminal with the C-terminal being free acid.

Considerations for choosing a means for removing particle aggregates from a filtration membrane include, but are not limited to, whether linking groups employed such as, for example, Linker arms 1-4, need to be cleavable and what types of release chemistry are needed. Examples, by way of illustration and not limitation, are summarized in Table 2.

TABLE 2

Linker arms and removal methods

| Removal method | Linker arm 1 | Linker arm 2 | Linker arm 3 | Linker arm 4 |
|---|---|---|---|---|
| Punch | cleavable non-cleavable | non-cleavable | cleavable non-cleavable | cleavable |
| Extract | cleavable | non-cleavable | non-cleavable | cleavable |
| Filter | cleavable | cleavable | non-cleavable | cleavable |

With regard to the examples of Table 2, in most cases Linker arm 3 will not be cleavable since label particles can always remain on the carrier particle. In the punch removal method of Table 2, Linker arm 3 may be cleavable depending on considerations such as diameter of orifices of any equipment used in the processes, for example. In all instances in Table 2, Linker arm 4 should be cleavable as MS labels should be released from label particles. In both extraction and filtration removal methods, Linker arm 1 is cleavable so that particle aggregates may be removed. The agents that promote cleavage and the cleavable moieties of the linking groups should be different for each different population of target rare molecules and for each of the linker arms so that, for example, Linker arm 1 for each different population can be cleaved for removal and Linker arm 4 for each different population is not cleaved until the reaction mixture is in a vessel and ready to be subjected to magnetic separation. In this example, if the binding of label particles to the carrier particle occurs after removal from the membrane, unbound label particles can be removed by, for example, centrifugation, magnetic separation or filtration and the same cleavage agents and cleavable moieties may be employed to both Linker arm 1 and Linker arm 4.

Requirements for the filtration approach may differ because, in order to filter carrier particles, the average diameter of the holes of a membrane must be larger than the carrier particles. In this instance, both Linker arm 2 and Linker arm 1 may be required to be cleaved at the same time. Of the three removal methods discussed above, the punch approach has the lowest risk as it reduces background, eliminates all risk of loss of particles and reduces the number of steps. The punch out approach also only requires one type of release chemistry, that is, one type of cleavable moiety and one type of cleavage agent. In order to accomplish any of these options for removal from the membrane, the membrane should be removed from any surface on which the membrane sits such as, for example, a microfluidic slide.

Figure 12:
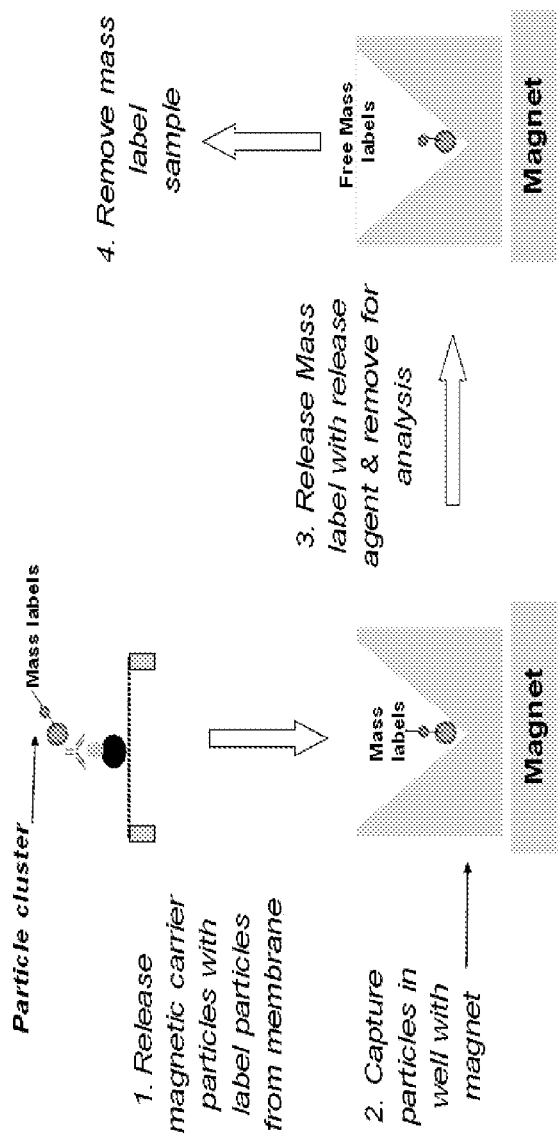
FIG. 12 is a depiction of an example of a method of removing particles from a membrane and sampling particles for analysis according to an example in accordance with the principles described herein.

As mentioned above, the carrier particles may be magnetic, which provides for a method for removing particles and preparing for analysis by MS. Referring to FIG. 12, a particle cluster is formed in a manner as described above on a membrane of a filtration device. The carrier particles of the particle cluster are linked to the capture antibody using Linker arm 1 that has a cleavable linkage. The particle cluster is treated with a first alteration agent for cleaving the cleavable linkage to release the magnetic carrier particles having attached thereto label particles with MS labels. The carrier particles have an average diameter that allows the cleaved carrier particles to pass through the pores of the membrane, which retains the larger diameter cell or capture particle having the target rare molecule attached thereto. The released magnetic carrier particles are retained in a suitable vessel where a magnet is employed to assist in releasing the magnetic carrier particles from the membrane and retaining the magnetic carrier particles in the vessel. A second alteration agent is employed to release the MS label from the label particles of the magnetic carrier particles in the vessel. The magnet assists in retaining the magnetic carrier particles in the vessel, from which the released MS labels are removed and subjected to MS analysis.

The methods described herein involve trace analysis, i.e., minute amounts of material on the order of 1 to about 100,000 copies of rare cells or target rare molecules. Since this process involves trace analysis at the detection limits of the mass spectrometers, these minute amounts of material can only be detected when detection volumes are extremely low, for example, $10^{-15}$ liter, so that the concentrations are within the detection. Given evaporation is likely and that "all" of the mass label must be removed must be removed for detection of 1 cell, unamplified methods are unlikely. "All" means that 100% of the MS label carrier particles would be needed to detect one rare cell or target rare molecule. The methods described herein involve trace analysis by amplification, i.e., converting the minute amounts of material to the order of about $10^7$ to about $10^{10}$ copies of every rare cell or target rare molecule. In this case only substantially all of the carrier particles for each cell or capture particle should be recovered to allow concentrations within the detection limits at reasonable detection volumes of, e. g., about $10^{-6}$ liter. The phrase "substantially all" means that at least about 70 to about 99% measured by the reproducibility in amounts of MS label released for a rare cell or a target rare molecule. Reproducible release is directly related to the formation and complete recovery of the carrier and label particles with a low variance of about 1 to about 30%.

Obtaining reproducibility in amounts of MS label or MS label precursor released for a rare cell or a target rare molecule requires measuring the formation and essentially complete recovery of the carrier and label particles. Therefore, in one approach the carrier particles, label particles, linking group and/or MS label or MS label precursor may be made fluorescent by virtue of the presence of a fluorescent molecule such as, but not limited to, FITC, rhodamine compounds, phycoerythrin, phycocyanin, allophycocyanin, o-phthaldehyde, fluorescent rare earth chelates, amino-coumarins, umbelliferones, oxazines, Texas red, acridones, perylenes, indacines such as, e.g., 4,4-difluoro-4-bora-3a, 4a-diaza-s-indacene and variants thereof, 9,10-bis-phenylethynylanthracene, squaraine dyes and fluorescamine, for example. A fluorescent microscope may then be used to determine the location of the carrier particles, label particles, linking group, and/or MS label or MS label precursor before and after treatment. This serves as a confirmative measure of the system function and is valued for additional information on the location of the rare cell or target rare molecule on the cellular structure or a capture particle.

Additional Embodiments

Some examples in accordance with the principles described herein are directed to methods of detecting one or more different populations of target rare molecules in a sample suspected of containing the one or more different populations of rare molecules and non-rare molecules. The concentration of the one or more different populations of target rare molecules is enhanced over that of the non-rare molecules to form a concentrated sample, which is incubated with, for each different population of target rare molecules, a mass spectrometry (MS) label precursor and an alteration agent that facilitates the formation of an MS label from the MS label precursor. Either the MS label precursor or the alteration agent is part of an affinity agent that is specific for a target rare molecule of one of the populations of the target rare molecules. The MS label corresponds to one of the populations of target rare molecules. A retentate and a filtrate are formed by contacting the incubated sample with a porous matrix. One or both of the retentate and the filtrate are subjected to MS analysis to determine the presence and/or amount of each different MS label. The presence and/or amount of each different MS label are related to the presence and/or amount of each different population of target rare molecules in the sample.

Some examples in accordance with the principles described herein are directed to methods of detecting one or more different populations target rare cells in a blood sample suspected of containing the one or more different populations of rare cells and non-rare cells. The concentration of the one or more different populations of target rare cells is enhanced over that of the non-rare cells to form a concentrated sample, which is incubated with, for each different population of target rare cells, an MS label precursor and an alteration agent that facilitates the formation of an MS label from the MS label precursor. Either the MS label precursor or the alteration agent is part of an affinity agent that is specific for a target rare cell of one of the populations of the target rare cells. Each different MS label corresponds to one of the populations of target rare cells. A retentate and a filtrate are formed by disposing the concentrated sample on a side of a porous matrix and applying vacuum to the disposed concentrated sample. One or both of the retentate and the filtrate are subjected to MS analysis to determine the presence and/or amount of each different MS label, and the presence and/or amount of each different MS label is related to the present and/or amount of each different population of target rare cells in the sample.

Some examples in accordance with the principles described herein are directed to methods of one or more different populations of non-cellular target rare molecules in a blood sample suspected of containing the one or more different populations of rare molecules and non-rare molecules. The blood sample is combined with one or more particle reagents. Each particle reagent comprises a binding partner for the non-cellular target rare molecule of each of the populations of non-cellular target rare molecules to form particle-bound non-cellular target rare molecules. The blood sample is subjected to a filtration procedure for enhancing the concentration of the one or more different populations of the particle-bound non-cellular target rare molecules over that of the non-rare molecules to form a concentrated sample, which is incubated with, for each different population of non-cellular target rare molecules, an MS label precursor and an alteration agent that facilitates the formation of an MS label from the MS label precursor wherein either the MS label precursor or the alteration agent is part of an affinity agent that is specific for a non-cellular target rare molecule of one of the populations of the non-cellular target rare molecules. The MS label corresponds to one of the populations of non-cellular target rare molecules. The concentrated sample is disposed on a side of a porous matrix and pressure is applied to the disposed concentrated sample to form a retentate and a filtrate. One or both of the retentate and the filtrate are subjected to MS analysis to determine the presence and/or amount of each different MS label, and the presence and/or amount of each different MS label is related to the present and/or amount of each different population of non-cellular target rare molecules in the sample.

Kits for Conducting Methods

The reagents for conducting a method in accordance with the principles described herein may be present in a kit useful for conveniently performing the method. In one embodiment a kit comprises in packaged combination modified affinity agents, one for each different target rare molecule. The kit may also comprise one or more unlabeled antibodies or nucleic acid probes directed at non-rare cells so that they can be eliminated from analysis. Depending on whether the modified affinity agent comprises an MS label precursor or an alteration agent, the kit may also comprise the other of the MS label precursor or the alteration agent that is not part of the modified affinity agent. The kit may also include a substrate for a moiety that reacts with an MS label precursor to generate an MS label. In addition, the kit may also comprise one or more of a fixation agent, a permeabilization agent, and a blocking agent to prevent non-specific binding to the cells, for example. Other reagents for performing the method may also be included in the kit, the nature of such reagents depending upon the particular format to be employed. The reagents may each be in separate containers or various reagents can be combined in one or more containers depending on the cross-reactivity and stability of the reagents. The kit can further include other separately packaged reagents for conducting the method such as ancillary reagents, binders, containers for collection of samples, and supports for cells such as, for example, microscope slides, for conducting an analysis, for example.

The relative amounts of the various reagents in the kits can be varied widely to provide for concentrations of the reagents that substantially optimize the reactions that need to occur during the present methods and further to optimize substantially the sensitivity of the methods. Under appropriate circumstances one or more of the reagents in the kit can be provided as a dry powder, usually lyophilized, including excipients, which on dissolution will provide for a reagent solution having the appropriate concentrations for performing a method in accordance with the principles described herein. The kit can further include a written description of a method utilizing reagents in accordance with the principles described herein.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following examples further describe the specific embodiments of the invention by way of illustration and not limitation and are intended to describe and not to limit the scope of the invention. Parts and percentages disclosed herein are by volume unless otherwise indicated.

EXAMPLES

All chemicals may be purchased from the Sigma-Aldrich Company (St. Louis Mo.) unless otherwise noted.

ABBREVIATIONS $K_3$EDTA=potassium salt of ethylenediaminetetraacetate
HRP=horse radish peroxidase ALP=alkaline phosphatase
WBC=white blood cells
RBC=red blood cells
EGFR=epidermal growth factor receptor
HUVEC=human umbilical vein endothelial cells
BSA=bovine serum albumin
HEPES=4-(2-hydroxyethyl)piperazine-1-ethanesulfonic acid
TRIS=2-amino-2-hydroxymethyl-propane-1,3-diol
ELISA=enzyme-linked immunosorbent assay
DAPI=4',6-diamidino-2-phenylindole
DMSO=dimethylsulfoxide (ThermoFisher Scientific)
min=minute(s)
μm=micron(s)
mL=milliliter(s)
mg=milligrams(s)
μg=microgram(s)
PBS=phosphate buffered saline (3.2 mM $Na_2HPO_4$, 0.5 mM $KH_2PO_4$, 1.3 mM KCl, 135 mM NaCl, pH 7.4)
mBar=millibar
w/w=weight to weight
RT=room temperature
hr=hour(s)
QS=quantity sufficient
IRB=Institutional Review Board
ACN=acrylonitrile
TFA=trifluoroacetic acid
CHAPS=3-[(3-cholamidopropyl)dimethylammonio]-1-propanesulfonate
TCEP=tris(2-carboxyethyl)phosphine hydrochloride (Sigma-Aldrich)
SPDP=N-Succinimidyl 3-(2-pyridyldithio)propionate)
MS=molecular weight
Ab=antibody
mAb=monoclonal antibody
vol=volume
MW=molecular weight
wt.=weight
PCR=polymerase chain reaction Example 1. Detection of Cell-Bound Target Rare Molecules Blood samples (about 10 mL) were collected from patients following an IRB approved protocol using Blood Collection Tubes and tube holders containing $K_3$EDTA and 0.45 ml TRANSFIX® (Vacutest Kima, Italy, TVT-09-50-45). Tubes were inverted 10 times after collection and were used directly after 1 h from collection. The samples were stored at RT for up to 5 days before isolation. Blood sample was added to a 50 mL centrifuge tube and QS to 20 mL with PBS solution. The SKBR lung cancer cell line (ATCC) was used to test the response of the assay. The SKBR lung cancer cells were added 0 to 1,000 cell counts per blood tube.

Within 5 days after storage at 25° C., the blood samples were filtered through a membrane having an average pore size of 8 μm according to a method disclosed in U.S. Patent Application Publication No. 2012/0315664, the relevant portions of which are incorporated herein by reference. During filtration, the sample on the membrane was subjected to a negative mBar, that is, a decrease greater than about −30 mBar from atmospheric pressure. The vacuum applied varied from 1 to −30 mBar as the volume of the sample reduces during filtration. High vacuum drops were allowable dependent on reservoir and sample volume and filtration rate. Just prior to filtration, a sample (7-10 mL) was transferred to a 50 mL FALCON® tube, which was filled to 20 mL with cold PBS with 0.2 to 10 mg/L fibrin added. The diluted sample was placed into the filtration station without mixing and the diluted sample was filtered through the membrane using a filtration system as described in U.S. Patent Application Publication No. 2012/0315664, the relevant disclosures of which are incorporated herein by reference. Following the filtration, the membrane was washed with PBS, and the sample was fixed with formaldehyde, washed with PBS, subjected to permeabilization using of 0.2% TRITON® X100 in PBS and washed again with PBS. Hydrogen peroxide (3%) incubation for 30 min was optionally used for removal of endogenous peroxidase activity, which can enhance specificity when HRP is used as an alteration agent.

Example 1A

In one example, cells captured on the membrane were detected with an affinity agent that was an antibody for HER2nue for rare cancer target molecule of the rare cells, to which HRP was attached. This antibody was obtained from Siemens Healthcare Diagnostics (Elkhart IN). A blocking buffer of 10% casein in PBS was dispensed on the membrane. After an incubation period of 5 min, the membrane was washed with PBS to block non-specific binding to the membrane. Next, an antibody-conjugate mix was dispensed to the membrane followed by an incubation period of 20 min at RT. The antibody conjugates (in 10% casein in PBS) at 15 μg/mL used in this example included anti-cytokeratin antibodies conjugated to horse radish peroxidase (HRP) (Siemens Healthcare Diagnostics Inc., Elkhart, Ind.), which detect H cytokeratin rare molecule. Unbound antibody was washed away with PBS+0.05% TWEEN® 20. The MS label precursor was o-phenylenediamine dihydrochloride (OPD) at 108.14 Da.

The MS label precursor reaction was carried out by the inclusion in the medium of a moiety (in this example, the MS label precursor OPD) to form the MS label at 108.14 daltons with two hydrogens being removed from OPD in the presence of HRP (alteration agent) on the membrane. In this example, 100 μL OPD (0.4 mg/mL) was obtained as a tablet set dissolved in 20 mL deionized water that yields a ready-to-use buffered solution and urea hydrogen peroxide (0.4 mg/mL) in 50 mM phosphate citrate buffer at pH 5.0 (Sigma Aldrich, SIGMAFAST OPD Tablets). In other examples, 10 μL L-tyrosine or 10 μL poly-L-tyrosine (100 μg/10 μL in SSC), 100 μL OPD (0.4 mg/mL in SSC) and 10 μL of $H_2O_2$ (Sigma 325-100 diluted to 0.00015% into SSC) were used.

The membranes with captured cells and treated with antibody for HER2nue conjugated to HRP were placed face up in cell culture plates (Costar 6 well 3506). PBS (200 μL) was added and the plates were sealed with adhesive lids and sonicated for 4 min at 40% amplitude Q sonic using 500 Watt and 20 Hz using a ¾ inch probe place within 1 mm from the bottom of the plate. After sonication, 150 μL was removed as the sample. A 10-μL aliquot of the sonicated sample was reacted with 10 μL of OPD solution. In another example, a positive vacuum was applied to the membrane so that liquid remained on the surface of membrane and 50 μL of the OPD solution was added. The reaction was allowed to occur for 10 min at a fixed temperature of 37° C. In both examples, the reaction mixture was removed and subjected to MS analysis using a mass spectrometer (BRUKER AUTOFLEX®, Bruker Corporation, Coventry, England). The MS label at the mass of OPD lacking two hydrogen atoms was detected and the relative abundance was accurately related to the presence and/or amount of HER2nue rare cancer target molecule in the sample when the sample was blood and when the sample was buffer. The method was able to detect HER2nue when only 1 cell was on the membrane down to 1,000 copies or 8.3 fM. Results were similar for both buffer and blood samples and were not subject to background interference from blood.

Example 1B

In another example, lung cancer cells (H226, ATCC) captured on the membrane were detected with affinity agent that was a nucleic acid for EGFR for rare cancer target molecule in the rare cells to which HRP was attached. The nucleic acid for EGFR was obtained from Dako North America Inc., Carpinteria Calif. The affinity agent was detected with 10 μL fluorochrome-labeled (Texas Red, Rhodamine) probe (HER FISH® probe mix, Dako). Samples were pipetted onto the area of the slide to be hybridized, a coverslip was applied immediately and sealed, and the slides were heated to 82° C. for 5 min. The reagent is in liquid form in hybridization solution containing 45% formamide, 10% dextransulphate, 0.21% N-methyl-2-pyrrolidone, 300 mmol/L NaCl, 5 mmol/L phosphate, and a blocking agent. The combination was then incubated overnight at 60° C. in an oven. Post-hybridization washes were done at RT twice with saline-sodium citrate buffer (SSC) and 0.3% NP-40 nonyl phenoxypolyethoxyethanol) to remove unbound probe. In this example, a biotinylated antibody for Rhodamine (Vector Laboratories, Burlingame Calif.) was used with streptavidin conjugated HRP, to provide attachment of the HRP catalyst to the affinity agent probe. In another example, HRP was directly conjugated to EGFR probe. In this example, the MS label precursor was OPD at 108.14 Da.

The MS label precursor reaction was carried out by the inclusion in the medium of a of the MS label precursor (in this example, OPD) to form the MS label in the presence of HRP (the alteration agent) on the membrane. In this example, 100 μL OPD was added to the membrane. A positive vacuum was applied to the membrane so that liquid remained on the surface of membrane. The reaction was allowed to occur for 1 to 60 min at a fixed temperature of 20° C. to 60° C., and in some examples, 37° C. After completion of the reaction, an aliquot of the reaction mixture was removed and subjected to MS analysis using the BRUKER AUTOFLEX® mass spectrometer. The MS label was detected and was accurately related to the presence and/or amount of the target lung cancer cells H226 in the sample. As in the previous example, the method was able to detect down to only a few cells (1-5 cells/tube) in both buffer and blood samples and was not subject to background interference from blood. The MS label at the mass of OPD lacking two hydrogen atoms was detected and the relative abundance was accurately related to the presence and/or amount of EGFR rare cancer target molecule in the sample when the sample was blood and when the sample was buffer. The method was able to detect EGFR when only 1 cell was on the membrane down to a few DNA copies in the cell. Results were similar for both buffer and blood samples and were not subject to background interference from blood.

Example 1C

In another example, lung cancer cells (H226 ATCC) captured on a membrane were detected using multiple affinity agents that were antibodies for multiple rare cancer target molecules of the rare cells. A blocking buffer of 10% casein in PBS was dispensed on the membrane. After an incubation period of 5 min, the membrane was washed with PBS to block non-specific binding to the membrane. Next, an antibody-conjugate mix (multiple affinity agents) was dispensed to the membrane followed by an incubation period of 20 min at RT. The antibody conjugates (in 10% casein in PBS) at 15 μg/mL used in this example included multiplexed anti-cytokeratin-19, anti-vim antibodies, and anti-cytokeratin-18 (Siemens, Elkhart, Ind.) conjugated to three different MS label precursors (Siemens, Elkhart, Ind.), and were used to detect each different target molecule separately. In this example, the MS label precursors were MS labels conjugated to the affinity agents by a peptide linkage. Unbound antibody was washed away (PBS+0.05% TWEEN® 20). Mass labels were released by placing face up in cell culture plates (Costar 6 well 3506) adding 200 μL of PBS, plates were sealed with adhesive lids and were sonicated for 4 min at 40% amplitude Q sonic using 500 Watt and 20 Hz ¾ inch probe from the bottom and 150 μL removed as the sample. A 5-μL aliquot of the sonicated sample was removed and subjected to MS analysis using the Bruker AUTOFLEX® mass spectrometer. The MS labels were fragmented by ionization and were detected and the relative abundance was monitored. The results were accurately related to the presence and/or amount of each of the target molecules of the lung cancer cells H226 in the sample. The method was able to detect down to only a few cells in both buffer and blood and was not subject to background interference from blood. Similar results were noted for each of the three biomarkers with separate mass labels.

Example 2. Detection of Non-Cell-Bound Target Rare Molecules

Blood samples of about 10 mL were collected from patients following an IRB approved protocol using Blood Collection Tubes and tube holders containing $K_3EDTA$ and 0.45 ml TRANSFIX® (Vacutest Kima TVT-09-50-45). Tubes are inverted 10 times after collection and can be used directly after 1 h from collection. Blood sample was added to a 50 mL centrifuge tube and QS to 20 mL with PBS solution. The HER2nue antigen was generated by lysis of SKBR cells to test the response of the assay. The HER2nue antigen was added at 0 to 1,000 lysed cell counts per blood tube.

Within 5 days after storage at 25° C., the blood samples were filtered through a membrane having an average pore size of 8 μm according to a method disclosed in U.S. Patent Application Publication No. 2012/0315664, the relevant portions of which are incorporated herein by reference. During filtration, the sample on the membrane was subjected to a negative mBar, that is, a decrease greater than about −30 mBar from atmospheric pressure. The vacuum applied varies from 1 to −30 mBar as the volume of the sample reduces from during filtration. High vacuum drops were allowable depending on reservoir volume and sample volume and filtration rate. Just prior to filtration, a sample (7-10 mL) was transferred to a 50 mL FALCON® tube, which was filled to 20 mL with cold PBS with 0.2 to 10 mg/L fibrin added. The diluted sample was placed into the filtration station without mixing and the diluted sample was filtered through the membrane. Following the filtration, the membrane was washed with PBS, and the sample was fixed with formaldehyde, washed with PBS, subjected to permeabilization using of 0.2% TRITON® X100 in PBS and washed again with PBS. Hydrogen peroxide (3%) incubation for 30 min was used in some examples for removal of endogenous peroxidase activity, which can help the specificity of when HRP is used as the catalyst.

In this example, anti-HER2nue antibody-biotin:streptavidin-dendrimer (Siemens, Elkhart, Ind. Clone NB-3) was made by mixing HER2nue-biotin (0.040 mg/mL or 0.25 μM) with streptavidin-dendrimer (0.428 mg/mL or 14.45 μM) in 25 mM TRIS, 25 mM HEPES, 3.75% BSA, 0.1M NaCl, 10% Trehalose, 2.5 mM magnesium acetate and 0.5 mM zinc chloride adjusted to pH 7.5. The anti-HER2nue antibody-biotin:streptavidin-dendrimer was captured on the membrane of the filtration device. A blocking buffer of 10% casein in PBS was dispensed on the membrane. After an incubation period of 5 min, the membrane was washed with PBS to block non-specific binding to the membrane. Next, a second HER2nue antibody (Siemens Elkhart, Ind. Clone TA-1), which was conjugated to a catalyst, was dispensed to the membrane followed by an incubation period of 20 min at RT. The second HER2nue antibody formed a sandwich complex with any circulating HER2nue antigen captured by the first antibody. The HER2nue antibody conjugates (in 10% casein in PBS) (affinity agents) at 15 μg/mL used in this example included antibodies conjugated to HRP and ALP, respectively, as the catalyst (Siemens, Elkhart, Ind.). Unbound antibody was washed away (PBS+0.05% TWEEN® 20).

MS label precursor reaction occurred in the next step by incubating the ALP on the membrane with 100 μL p-nitrophenyl phosphate (pNPP) substrate (Sigma, Catalog # N189) at 37° C. for 10 min. A positive vacuum was applied to the membrane so that liquid remained on the surface of membrane. The reaction was allowed to occur for a period of time (1 to 60 min) at a fixed temperature 20° C. to 60° C., in some examples, 37° C. After completion of the reaction an aliquot of the reaction was removed and measured on the BRUKER AUTOFLEX® mass spectrometer. Reaction of pNPP catalyzed by ALP results in removal of phosphate to form a phenolic alcohol. The phenolic alcohol MS labels were detected directly by the mass difference. The method was tested when the sample was blood and when the sample was buffer. The method was able to detect down to only a few cells in both buffer and blood samples and was not subject to background interference from blood.

Control not in Accordance with the Principles Described Herein.

Optical ELISA sandwich immunoassay for Her2nue of SKBR lysated cells was also performed as a comparative control. Blood samples of about 10 mL were collected from patients following an IRB approved protocol using Blood Collection Tubes and tube holders containing $K_3$EDTA and 0.45 ml TRANSFIX® (Vacutest Kima TVT-09-50-45). Tubes were inverted 10 times after collection and were used directly after 1 h from collection. Blood sample was added to a 50-mL centrifuge tube and QS to 20 mL with PBS solution. The HER2nue antigen was generated by lysis of SKBR cells to test the response of the assay. The HER2nue antigen was added at 0 to 20,000 lysed cell counts per blood tube.

Within 5 days after storage at 25° C., the blood samples were filtered through a membrane having an average pore size of 8 μm according to a method disclosed in U.S. Patent Application Publication No. 2012/0315664, the relevant portions of which are incorporated herein by reference. During filtration, the sample on the membrane was subjected to a negative mBar, that is, a decrease greater than about −30 mBar from atmospheric pressure. The vacuum applied varies from 1 to −30 mBar as the volume of the sample reduces during filtration. High pressure drops were allowable depending on reservoir volume and sample volume and filtration rate. Just prior to filtration, a sample (7-10 mL) was transferred to a 50-mL FALCON® tube, which was filled to 20 mL with cold PBS with 0.2 to 10 mg/L fibrin added. The diluted sample was placed into the filtration station without mixing and the diluted sample was filtered through the membrane. Following the filtration, the membrane was washed with PBS; and the sample was fixed with formaldehyde, washed with PBS, subjected to permeabilization using of 0.2% TRITON® X100 in PBS and washed again with PBS. Hydrogen peroxide (3%) incubation for 30 min was used in some examples for removal of endogenous peroxidase activity, which aided specificity when HRP was used as the catalyst.

After filtration, a membrane with 0 to 0 20,000 SKBR cells was placed face up in cell culture plates with 200 μL of Tris-buffered saline (TBS) (50 mM Tris-Cl, pH 7.5, 150 mM NaCl). The mixture was sonicated for 4 min at 40% amplitude Q sonic for 500 Watt in 20 Hz. Sonication caused a lysate of Her-2nue to be removed from the membrane. Based on standards of counted lysed cells, there was 1.2 attomolar of Her-2nue per cell, which amounted to 1.46× $10^5$ molecules of Her2nue per cell. The lysate was removed in 75 μL duplicates for testing by optical ELISA.

The ELISA method was carried out by coating the plate at 5.8 μg/mL with anti-HER2nue antibody (Siemens, Elkhart, Ind. Clone NB-3). Each well of the plate was washed 5 times with 300 μL TBS. Blocking buffer of 10% Albumin in PBS was dispensed at 300 μL into each well and incubated at 35° C. for 1 h followed by washing 5 times with 300 μL TBS with 0.05% Tween 20 (T-TBS). The sample of lysate was applied to the well and incubated at 35° C. for 1 h followed by washing 5 times with 300 μL T-TBS. Next, a second HER2nue antibody (Siemens Elkhart, Ind. Clone TA-1), which was conjugated to ALP or HRP as catalyst, in TBS at 0.5 μg/mL was dispensed at 300 μL into each well followed by an incubation period of 60 min at 35° C. The second HER2nue antibody formed a sandwich complex with any circulating HER2nue antigen captured by the first antibody. Unbound antibody was washed away with 5 washes with 300 μL T-TBS. Standards with known lysates were used to calibrate the assay.

The optical reaction occurred in the next step by reacting the HRP in the ELISA with 100 μL of OPD. The reaction mixture was incubated at 37° C. for 10 min. Alternatively, 100 μL of 3,3',5,5'-tetramethylbenzidine (TMB) substrate (Pierce Chemical Company, Dallas Tex., Catalog #34038) was incubated at 37° C. for 10 min followed by addition of 50 μL of 1.8 M sulfuric acid to quench color. For ALP as the alteration agent, ALP on the affinity agent on the membrane was combined with 100 μL pNPP substrate (Sigma, Catalog # N189) and incubated at 37° C. for 10 min. Results are shown in Table 3.

TABLE 3

Optical detection of Non-Cell bound target rare molecules

| Optical OP data for ALP | | | Optical TMB data for HRP | | |
| --- | --- | --- | --- | --- | --- |
| Cell/well | RU | % CV | Cell/well | RU | % CV |
| 12727 | 35.9 | 0.00% | 1654 | 130.9 | 0.02% |
| 5170 | 25.3 | 0.02% | 708 | 61.1 | 0.02% |
| 2365 | 9.3 | 0.00% | 381 | 34.5 | 0.03% |
| 635 | 2.8 | 0.00% | 81 | 12.5 | 0.05% |
| 0 | 1.1 | 0.07% | 0 | 8.9 | 0.03% |

The ELISA method was able to detect 381-2365 lysed cells in buffer but could only detect 10,000 cells in blood as the optical method was not specific and all indicators OPD, PPNP, and TMB gave background higher than the response for 9,000 cells. Optical enzymatic detection was insensitive and not specific; therefore, it was surprising that the same enzyme and indicator could be used with mass detection and filtration.

Example 3. Particle Detection of Rare Cells and Target Rare Molecules

Figure 11:
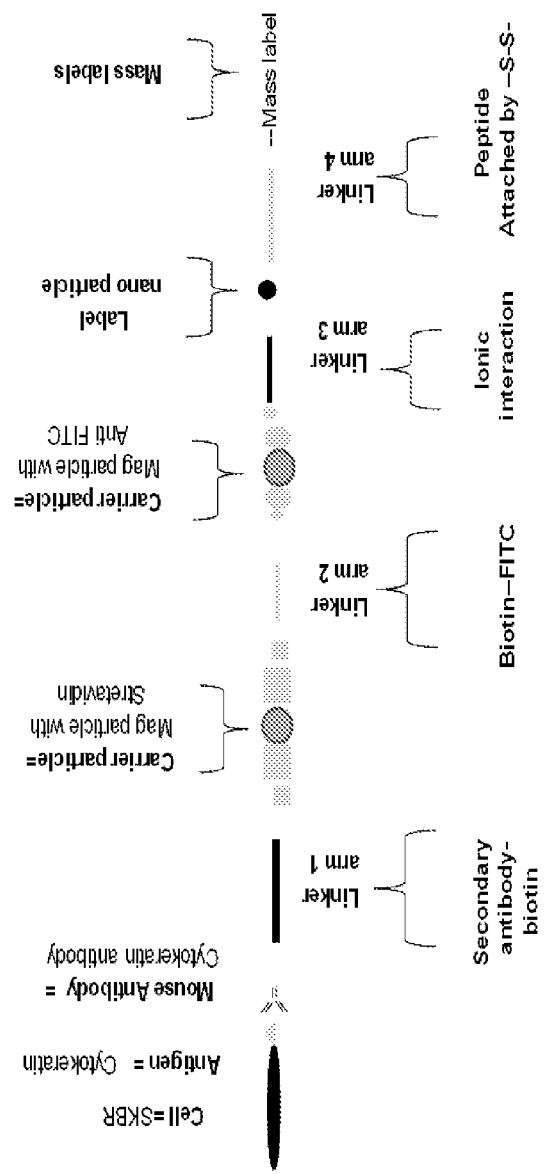
FIG. 11 is a depiction of an example of particle amplification reagent according to an example in accordance with the principles described herein.

FIG. 11 depicts the particle detection method used in this example, by way of illustration and not limitation, using a particle amplification reagent (as described above in FIG. 10) in accordance with the principles described herein. The linker arms are set forth in FIG. 11 with the following characteristics: cleavable for Linker arm 1, not cleavable for Linker arm 2, cleavable for Linker arm 3, and cleavable for Linker arm 4. The materials used for this example were from Sigma-Aldrich Corporation (St. Louis Mo.) unless otherwise indicated. Antibody conjugates were prepared by standard bioconjugation techniques such as described by Greg T. Hermanson in Bioconjugate Techniques, Third Edition 2013, Elsevier Inc., 225 Wyman Street, Waltham Mass. Peptides were prepared by standard peptide synthesis techniques such as described by Michael W. Pennington and Ben M. Dunn in Peptide Synthesis Protocols, Edition 1, November 1994, Springer-Verlag, New York, LLC, New York N.Y. Materials are shown in Table 4 along with common terms used in the description for the material.

TABLE 4

```
Spray solvent = 50% ACN HPLC with 0.1% vol TFA

DTT = Pierce DTT 7.7 mg/tube (ThermoFisher Scientific Inc., Waltham MA)

PBS tablets = Phosphate Buffered Saline tablets (add 1 tablet to 200 mL water)

HCCA matrix = α-cyano-4-hydroxycinnamic acid 5 mg/mL (10 mg/1.5 mL) in ACN HPLC with
0.1% vol TFA (Bruker Corporation, Billerica MA)

Avidin Mag carrier particle = Streptavidin-coated SERA-MAG ® magnetic particles, 1%, 0.756 µM
(ThermoFisher Scientific Inc.)

Avidin Mag capture particle = Streptavidin-coated SERA-MAG ® magnetic particles, 1%, 10 µM
(ThermoFisher Scientific Inc.)

Anti FITC Mag particle = Magnetic particles conjugated to anti-fluorescein, 1%, 0.756 µM Biotin-FITC = Biotin-Fluorescein (MW 732.8) (ThermoFisher Scientific Inc.)

Biotin-Disulfide-FITC = a hetero-dimer of two 9-amino acid peptides linked by a disulfide bond
bridge bond between two cysteine residues where one N-terminus is conjugated to FITC
and the other N-terminus is conjugated to Biotin and has the following sequence:
Biotin-Ile-Gly-Met-Thr-Ser-Arg-Tyr-Phe-Cys-S-S-Cys-Phe-Tyr-Arg-Ser-Thr-Met-Gly-
Ile-FITC (SEQ ID NO: 1)

IC9-1 (label) = Ile-Gly-Met-Thr-Ser-Arg-Tyr-Phe-Cys (SEQ ID NO: 2) (MW 1077.3)

IC9-3 (standard) = Ile-Gly-Met-Gly-Ser-Arg-Tyr-Phe-Cys (SEQ ID NO: 3) (MW 1033)

IC9-2-FITC = FITC-Ile-Gly-Met-Thr-Ser-Arg-Tyr-Phe-Cys (SEQ ID NO: 4) (MW1408.9)

IC9-2-biotin = Biotin-Ile-Gly-Met-Thr-Ser-Arg-Tyr-Phe-Cys (SEQ ID NO: 5) (MW 1321.6)

Membrane washer = SWINNEX ® filter housing (EMD Millipore, Billerica MA)

Cancer cell antibody-peptide MS label conjugate =
CK8/18 Ab-Ile-Gly-Met-Thr-Ser-Arg-Tyr-Phe-Cys (SEQ ID NO: 6) (0.48 mg/mL in PBS
pH 7.4 and 0.1M NaN₂)

Cancer cell antibody-peptide-biotin mAb conjugate =
Biotin-Ile-Gly-Met-Thr-Ser-Arg-Tyr-Phe-Cys-CK8/18 Ab (SEQ ID NO: 7) (0.5 mg/mL
in PBS pH 7.4 and 0.1M NaN₂)

Secondary antibody-biotin = goat anti-mouse IgG biotin (whole molecule)-Biotin (0.6 mg/mL)

Rare molecule antibody for capture particle attachment =
FITC-Ile-Gly-Met-Thr-Ser-Arg-Tyr-Phe-Cys-HER2nue NB-3 antibody (SEQ ID NO: 8)
(0.5 mg/mL in PBS pH 7.4 and 0.1M NaN₂)

Rare molecule antibody for carrier particle attachment =
Biotin-Ile-Gly-Met-Thr-Ser-Arg-Tyr-Phe-Cys-Anti-HER2nue TA1 (SEQ ID NO: 9) (0.5 mg/mL
in PBS pH 7.4 and 0.1M NaN₂)

SKBR cells = SKBR3 human breast cancer cells (ATCC)

HER2nue lysate = $10^5$ SKBR3 cells were lysed by sonication. HER2nue lysates were prepared at
about 2 × $10^6$ SKBR3 cells/mL and assayed for HER-2/neu concentration using a
commercially available ELISA assay kit (Calbiochem QIA10-1EA-HER2nue ELISA
Kit, EMD Biosciences, Inc., USA). Data showed an average of about 2 × $10^4$ ng/mL Her-
2neu per cell in cell lysates or 44551 copies of Her-2Neu per cell.
```

TABLE 4-continued

```
Silica amine label particle = Propylamine-functionalized silica nano-particles 200 µm,
mesoporous pore sized 4 nm Dendrimer label nanoparticle = PAMAM dendrimer, ethylenediamine core, generation 5.0
solution 5 wt. % in methanol, 96 surface amine groups, nano-particles 7.0 nm diameter
and MW of 28826

Dendrimer label nanoparticle high density = PAMAM dendrimer, ethylenediamine core,
generation 7.0 solution 5 wt. % in methanol, 515 surface amine groups nano-particles SPDP = 50 mg stored at -20° C. (ThermoFisher Scientific Inc.)

Glass slide = FISHERBRAND ™ SUPERFROST ™ Plus Microscope Slides (ThermoFisher
Scientific Inc.)

Blocking agent = Casien, the blocking solution (Candor Biosience GmbH, Allgau Germany)

NHS-FTIC = NHS-Fluorescein Antibody Labeling Kit (ThermoFisher Scientific Inc.)

NHS-Biotin = EZ-LINK ™ Sulfo-NHS-LC-Biotin (ThermoFisher Scientific Inc.)

Membrane = WHATMAN ® NUCLEOPORE ™ Track Etch membrane, 25 mm diameter and 8.0 µM
pore size Magnet for PCR well = 384 magnetic post stand for PCR plate (Alpaqua Engineering, LLC,
Beverly MA)

PCR well = 384 well PCR (ThermoFisher Scientific Inc.)

Magnet for micro-centrifuge tubes = Dynal MPCS for microcentrifuge tubes (Dynal Biotech
ASA, Norway)
```

Step One. Peptide Mass Label and Standard Calibrator Preparation

Peptide MS labels and internal standards were selected. The number of amino acids was varied of for labels and internal standard tested. In this example, the peptide MS labels and internal standards both contained 9 amino acids and varied by 1 amino acid having a mass difference of 45 daltons. This example was optimized for detection using MALDI. Similar data was obtained using labels and internal standards of three amino acids and ESI. The peptide labels were prepared by standard amino acid conjugation techniques.

Peptide MS labels were weighed out as 10 mg solid peptide MS label (IC9-1 MW of 1077 daltons) and peptide internal standard (IC9-3 MW of 1033 daltons into separate 10 mL volumetric flasks and were diluted with 50% ACN/water and 0.1% TFA diluent. Working solutions for label and standard were made at 1 mg/L by diluting 100 µL of stock solution with 99.9 mL of 50% ACN/water and 0.1% TFA diluent. Ammonium bicarbonate (200 mg) (0.1% w/w, 200 mg CHAPS (0.1% w/w) (CHAPS solution) and one PBS tablet into 200 mL nano-pure water. The measured pH was 7.46. Calibrators were made using working solution for label, internal standard and 1 mL CHAPS solution with 50% ACN/water and 0.1% TFA as diluent according to Table 4 below in a 10 mL volumetric flask at 0, 50, 100, 200, 300 and 400 µg/L for label, and 200 µg/L internal standard.

Step Two. Mass Analysis by MALDI

A matrix solution was made using 10 mg/α-cyano-4-hydroxycinnamic acid in 1.5 mL of 50% ACN/50% $H_2O$/0.1% TFA solvent. The MALDI instrument was used in reflector mode, positive ionization in the 700-3500 Da range (Reflector mode from a mass of 700 Daltons to 3500 Daltons) with 2500 shots taken (100 frequency) using a polished steel target plate (MTP 384). The procedure for analysis included cleaning the target plate with isopropanol and then water, sonicating for 10 minutes in isopropanol, followed by 10 min. in 30% ACN/70% $H_2O$/0.1% TFA solvent, and then drying with nitrogen or air.

A 10 µL Gilson piston pipette with CP10 tips was employed. First, 1.5 µL of calibrator was placed on target. Before significant evaporation (within a few minutes) 1.5 µL of matrix was placed on sample targets. Replicates were prepared for targets and included a blank row and spot between each target and were allowed to air dry over 15 min. Target was placed in the MALDI instrument for testing. A calibration curve was prepared using label peptide to internal standard peptide standard ratio plotted against the concentration of the label peptide to provide a calibration curve. The CV for any level was <10%. Limit of quantitation for the IC 9-1 peptide was 50 µg/L (50 ng/mL).

Step Three. Demonstration of Peptide Release

Cancer cell antibody-peptide biotin conjugate was produced by conjugating peptides via S—S bond between the cysteine of the MS label peptide and the antibody using N-succinimidyl 3-(2-pyridyldithio) propionate (SPDP). The conjugated materials were tested to determine the amount of peptide conjugated and to demonstrate cleave of this linker group by TCEP or DTT as the alteration agent. The amount of peptide in the conjugate was calculated by using MW of conjugate of 168,300, the concentration of conjugate of 0.48 mg/mL, the MW of free IC9-2-biotin peptide conjugate of MW 1321.6. Therefore 0.48 mg/mL×1321/168300=0.0038 mg/ml free peptide. Therefore 5 µL of the cancer cell antibody-peptide biotin conjugate solution when diluted in 100 µL of water should provide 188 µg/L of IC9-2-biotin peptide conjugate.

The mass alteration agent was made by making a 1 mg/ml TCEP stock solution in nano-pure water by weighing 10 mg TCEP into 10 mL nano pure water. Alternatively, 500 mM DTT stock solution was prepared by adding 100 µL nano-pure water to 7.7 mg DTT. For quantitation of release, working stock solutions of IC9-3 internal standard entirely in water was prepared as TFA will inhibit release. Calibration as in Step One is repeated with IC9-2-biotin as the peptide label.

After adding 70 μL water into a polypropylene vial, followed by 5 μL of CK8/18 Ab:IC9-2-biotin and 5 μL of TCEP (diluted concentration of 50 μg/mL) or DDT (diluted concentration of 25 mM) and 10 μL of IC9-1 internal standard at 1 mg/L, release reaction occurred. The solution was incubated for 15 min at 70° C. and 1.5 μL was removed for analysis by MALDI as shown in Step 2. The observed released of IC9-2-biotin peptide conjugate was about 244 μg/L, thus supporting the target conjugation of 1.3 peptides per antibody; and complete release and formation of the IC9-2-biotin mass label was demonstrated.

Step Four. Label Particle Production

The label particle was prepared by conjugating peptides via S—S with SPDP to the silica amine label particle. A solution of 7.5 mg SPDP was made in 1.6 mL DMSO. The SPDP solution (25 μL) was added to 4 mg of propyl amine-functionalized silica ($4\times10^{11}$ particles) in 1.0 mL PBS and the mixture was incubated for 30 min at RT in a polypropylene vial with vigorous mixing using a roller mixer at 75 rpm. The vial was centrifuged (3 min at 2000 RPM using an EPPENDORF® Centrifuge #5417C) and unreacted materials were decanted. The label particles were washed twice with 1.0 ml PBS with centrifugation and decanting washes.

The MS label (IC9-1) (MW 1077.2) was attached to the label particle with a cleavable linker arm (S—S group in the linker arm) to make the MS label precursor by first making a IC9-1 solution of 8 mg in 1.0 mL PBS, followed by adding 200 μL of IC9-1 solutions to the washed SPDP activated particles, followed by adding 1.0 mL PBS to the polypropylene vial. The vial was incubated overnight at RT with vigorous mixing using a roller mixer at 75 rpm. The reacted label particles were washed twice with 1.0 ml PBS with centrifugation and decanting washes. MALDI analysis of the wash liquid after two washes did not detect any free IC9-1.

Step Five. Carrier Particles Loading with Label Particles

Label particles were associated to carrier particles through ionic binding between the carboxylic groups on the magnetic carrier particle and the amine groups of the silica label particle. This binding was strongly associated and served as a linkage group. There were two types of carrier particles made to demonstrate aggregating multiple carrier particles layers beyond the first layer associated to the cell by affinity agent.

Type 1 carrier particles were produced by associating approximately 100 label-particles per carrier particle by adding 1000 μL of PBS to the 4 mg of washed IC9-1 silica nano particles to make a solution at 4 mg/mL and mixing with 40 μL of Avidin Mag particle (1% by weight particle/water). This provided 0.04 mg of Mag particle containing 4 mg label particle or a 1:100 w/w of carrier to label particle ratio.

Type 2 carrier particles were produced by associating approximately 100 label-particles per carrier particle by adding 1000 μL of PBS to 4 mg of washed IC9-1 silica nano particles to make a solution at 4 mg/mL and mixing with 40 μL of FITC Mag particle (1% w/w particle/water). This provided 0.04 mg of Mag particle containing 4 mg label particle or a 1:100 w/w of carrier to label particle ratio.

The solutions of carrier particles were allowed to stand for a few minutes at RT and then added to a Dynal MPCS magnet for micro-centrifuge tubes. The magnetic particles stuck to the side of the tube. Any unbound label particles fell to the bottom. The waste of 1.0 mL of liquid is removed and an additional 1.0 mL of PBS was added and removed as a wash step. Nanoparticles on the bottom of the vial were not visible in either wash confirming mostly all of the nanoparticles were picked up or at least 100 particles per magnetic carrier particle.

An alternative linker arm was demonstrated by attachment of biotin or FITC to the label particle via non-cleavable linker arms providing a means to capture to the magnetic particle. Conjugation of biotin to the amine terminals of the label particle (2 mg/mL) was done using NHS-biotin [N-hydroxysuccinimidyl-6-(biotinamido) hexanoate] as the biotinylation reagent by stirring for 2 hr in phosphate buffer at pH 9.0 (100 mg borate in PBS). Conjugation of FITC to the amine terminals of the label particle (2 mg/mL) was done using NHS-fluorescein as the reagent by stirring for 2 hr in phosphate buffer at pH 9.0.

Another alternative linker arm was demonstrated by attachment of biotin or FITC to the label particle via a cleavable linker arm using SPDP to attach 10% IC-9-1-Biotin (MW 1321.6) or IC9-1 FITC at same time as 90% IC9-1 to allow a means to capture to the magnetic particle. This provided a cleavable linker arm between label and carrier particles.

The amount of mass label on the associated carrier and label particles was determined for the 4 mg/mL solution. A higher calibration curve for IC-9-1 mass label and IC-9-3 internal standard as in Step One is repeated at 0, 50, 100, 200, 300 and 400 μg/mL for label, and 100 μg/mL internal standard. The release of MS label was accomplished in the polypropylene vial by adding 80 μL water, 10 μL of IC 9-3 at 1 mg/mL (in water) (MW 1033, 1 mg/L) as internal standard and 10 μL of TCEP to the magnetic particles. The vial was incubated for 5 minutes at 70° C. and 1.5 μL was removed for analysis by MALDI (as in Step Two).

The results for loading of mass label peptide onto label particle was 0.18 mg/L or $2.8\times10^4$ copies of IC-9-1 mass label per label particle. There are $2.2\times10^6$ amines covering the surface of the 200 nm amine-coated silica nanoparticle of 200 nm diameter, thus, loading was 33%. The results for loading of label particle on to the carrier particle were 100 label particles per every carrier particle and supported the assumption of $10^4$ to $10^5$ MS labels per carrier particle. The results also demonstrated release of the MS label from the label particles associated with carrier particles.

Step Six. Cell Isolation and Affinity Reaction to Form Particle Cluster

Blood was collected from healthy donors (9 mL per donor) and stored in Transfix tubes for up to 5 days. The blood sample was spiked with SKBR3 cell using a stock to give 1772 cells/tube.

A rare cell filtration system (Siemens Healthcare Diagnostics Inc.) was used to isolate the cancer cells, perform affinity reactions and to load the carrier particles onto the cells. A procedure for cell isolation was used as disclosed in U.S. Patent Application Publication No. 2012/0315664, the relevant portions of which are incorporated herein by reference. During filtration, sample on the Membrane was subjected to a negative mBar, that is, a decrease greater than about −30 mBar from atmospheric pressure. The vacuum applied varied from 1 to −30 mBar as the volume of the sample reduces during filtration. The diluted sample was placed into the filtration station without mixing and the diluted sample was filtered through the Membrane. Following the filtration, the Membrane was washed with PBS, and the sample was fixed with formaldehyde, washed with PBS, subjected to permeabilization using of 0.2% TRITON®

X100 in PBS and washed again with PBS. A blocking step was employed in which blocking buffer of 10% casein in PBS was dispensed on the Membrane. After an incubation period of 5 min, the membrane was washed with PBS to block non-specific binding to the membrane. The blocking step and permeabilization step were performed for the first affinity reaction and not repeated for second and third affinity reactions. Five PBS TWEEN® surfactant washings were done after each affinity reaction. The rare cells were then measured using affinity reactions and immunocytochemistry (ICC) and/or in situ hybridization (ISH) methods.

For the ICC reaction, the first affinity reaction was done with 15 µg/mL of conjugate CK8/18 Ab-YC-9-3 peptide-biotin during the antibody incubation step and 10 µg/mL of streptavidin magnetic particles. The slide was incubated for 25 min prior to washing. Alternatively, the CK8/18 antibody was directly linked to the carrier particle. Alternatively, a secondary anti-mouse antibody linked to biotin was used to detect anti-mouse CK8/18 Ab.

Alternatively, ISH methods using a nucleic acid probe as the affinity partner for RNA or DNA were demonstrated with a probe containing a biotin and were performed according to the method previously disclosed in U.S. Patent Application Publication No. 20140235495 and PCT/US/2014/031895, the relevant disclosures of which are incorporated herein by reference. The ISH method was performed individually or in combination with ICC such that rare cells were targeted by both an antibody and a nucleic acid for enhanced detection.

A biotin-FITC solution was prepared by diluting 5 mg of biotin-FITC in 0.5 mL of DMSO to give a 10 mg/mL stock solution, where 50 µL of the biotin-FITC stock solution was mixed with 950 µL casein blocking solution to give a 0.5 mg/mL working solution. Alternatively, a biotin-peptide disulfide peptide FITC stock solution was mixed with 950 µL casein blocking solution to give a 0.5 mg/mL working solution of a cleavable linker arm. As FITC is fluorescent, the carrier particles and linker group are fluorescent and were visualizable under the microscope. Alternatively, it was demonstrated that FITC can be attached to the label particles and/or MS label.

Additional carrier particles loaded with MS label were added to the primary carrier particle by adding 7.5 µL of anti-FITC magnetic beads at 10 mg/ml coated with nanoparticles containing of IC-9-1 mass label (as produced in Step Four) (1 µM diameter size) with 50 µL of the biotin-FITC working solution to 320 µL solution of casein blocking buffer. Optionally, additional stepwise addition of 7.5 µL of anti-streptavidin magnetic beads at 10 mg/ml (1 µM diameter size) coated with nanoparticles containing of IC9-1 mass label (as produced in Step Four) followed by more additions of anti-FITC magnetic beads in stepwise fashion was done. The slide was incubated for 25 min prior to washing.

Once the affinity reaction and optional additional carrier particles reaction processes were completed, a DAPI staining step was completed after completing all washes. The slides were removed from the filtration unit, and the bottom of each slide was wiped clean. DABCO (24 µL) was dropped onto the Membrane, and a cover slip was carefully placed on top. Slides were analyzed by microscope. The area for a 40× image is 224 µm wide and 167 µm tall and measurements confirmed that that green dots are about 1 (note that a 20× image is 448 µm by 335 µm).

The number of magnetic particles observed under the microscope using the positive and negative controls is shown below in Table 5 and were less than 10 carrier particles per 40× image area for negative control and were 1109 carrier particles per cancer cell for positive sample. When only one type of carrier particle was used, namely, Mag-Strept (streptavidin-magnetic particles), there were 133 carrier particles per cancer cell, a lesser but potentially acceptable number of amplifications.

TABLE 5

| Sample | Anti-mouse IgG | Mag- Strept | Mag- anti FITC | Carrier particles per cancer cell |
|---|---|---|---|---|
| Negative control | 0 uL | 7.5 uL | 7.5 uL | 2 |
| Positive sample | 80 uL | 7.5 uL | 0 uL | 133 |
| Positive sample | 80 uL | 7.5 uL | 7.5 uL | 1109 |

Alternatively, examples were carried out using the following rare cells instead of cancer cells: circulating endothelial cells; circulating epithelial cells; mesochymal cells; fetal cells; immune cells (B cells, T cells, macrophages, NK cells, monocytes); stem cells; and immature granulocytes. All passed through the pores of the filtration device and were attracted to an antibody or probe as an affinity agent. The rare cells were detected in all cases.

Step Seven. Particle Removal and Mass Label Determination

Membrane was removed from the slide carefully with tweezers and placed in a well of the plate. The tweezers were first sprayed with ethanol and dried before using. Solvent (50% ACN/H$_2$O) (180 µL) was added to the well followed by 10 µL of a TCEP solution (1 mg/mL in 50% ACN/H$_2$O) and 10 µL of internal standard solution (prepared as described above). The plate is sealed with an adhesive lid and sonicated from the bottom of the plate for 4 min at 40% amplitude Q sonic using 500 Watt and 20 Hz ¾ inch probe. The sonicated sample was removed by pipette.

Alternatively, when the linker arm between the rare cell (or capture particle) was cleavable, 180 µL of solvent (50% ACN/H$_2$O mixture) was added to the top of the well, mixed by extracting in and out of the pipette tip at least 10 times and left to incubate for 20 min. The extracted sample was removed by pipette. Alternatively, the position of rare cell was located on the Membrane and the rare cell with particle cluster and the Membrane was punched out and the punched out Membrane was added to a 30 µL vial in the 384 well PCR. Alternatively, rare cells were picked up by a magnet and the magnet was added to a vial for liquid treatment with PBS. Alternatively, when the linker arm between the rare cell (or capture particle) was cleavable and the linker arm between the carrier particles was cleavable, the entire Membrane was removed and the label particles were washed into 200 µL water with applied vacuum or pressure.

Release with mass label (IC9-1) with alteration agent (TCEP) was demonstrated for punched out cells and measured against IC9-1 (MW 1077.3) as internal standard by adding 75 µL water to a polypropylene vail, 5 µL of TCEP (diluted concentration of 50 µg/mL) and 20 µL of IC-9-3 internal standard at 1 mg/L in water. A magnetic force was used to hold and isolate the magnetic capture particle.

After incubation for 15 min at 70° C., 1.5 µL was removed for analysis by MALDI as shown in Step Two. The observed released IC9-2-biotin peptide was 165 µg/L, thus supporting the detection of a single cancer cell. The above was repeated with 0, 3, 30 and 300 cells and a response curve was generated and the variance of result was less than 30% for 3 cells and less than 10% for 300 cells.

Step Eight. Capture Particle Option for Rare Molecule Detection

Step 5 was repeated with blood samples that were spiked with HER2nue as an example of a target rare molecule instead of SKBR cells. HER2nue antigen was prepared by sonication of SKBR3 cell to HER2nue lysates to produce 44551 copies of Her-2Neu per cell. HER2nue antigen was added at $2\times10^4$ ng/mL and $2\times10^2$ ng/mL to two blood samples.

A HER2nue NB-3 biotin antibody was used for affinity capture of the target rare molecules with avidin magnetic capture particles of 10 μm diameter. The blood samples were diluted into 20 mL of PBS buffer. The 300 μL of HER2nue NB-3 antibody (15 μg/mL) and 7.5 μL of avidin magnetic capture particles (10 mg/mL; 10 μM diameter size) were added to each positive sample and a negative control. The sample was incubated for 25 min prior to filtration. The sample was filtered and washed. The Avidin Mag capture particles were retained on the surface of the Membrane.

The first affinity reaction was done by adding 15 μg/mL of Her2nue antibody TA1 conjugated to FITC; 7.5 μL of anti-FITC magnetic carrier particles (10 mg/mL; 1 μM diameter size) coated with nanoparticles containing of IC9-1 mass label (as produced in Step Four) and 50 μL of the biotin-FITC working solution to the 320 μL solution of casein blocking buffer. The slide was incubated for 25 min prior to washing. A second HER2nue TA1 FITC antibody was used to make a sandwich with the target rare molecules and the carrier and label particles.

The remaining procedure was carried out as in Step Seven. The positive samples with Her2nue showed that the magnetic carrier particles of 1.0 μm did not pass through the filter and had Her2nue bound by both antibodies. The negative samples without Her2nue showed the magnetic carrier particles of 1.0 μm did pass through the filter and had Her2nue bound by both antibodies. The MS labels retained were detected as shown in Step Seven. The target rare molecule assay was able to detect and quantitate HER2nue at $2\times10^2$ ng/mL and less. Commercial ELISA HER2nue kit only detects at a level of $2\times10^4$ ng/mL.

Alternatively, examples of target rare molecules other than Her2nue were tested and included small bacteria, virus and cell-free nucleic acids, which can pass through the pores if not attracted to an affinity agent on the capture particle. To demonstrate the bacterial case, an anti-*E coli* polyclonal antibody from goats was used to detect single *E coli* as evidenced by microscopy of fluorescent magnetic carrier particles formed on the capture particle. The anti-*E coli* polyclonal antibody was attached to both carrier particles formed on the capture particle. Similarly, the viral case was demonstrated using an anti-influenza virus polyclonal antibody from rabbit to detect single influenza cells as evidenced by microscopy of fluorescent magnetic carrier particles formed on the capture particle. Cell free nucleic acids were demonstrated using silica-coated carrier particles. Silica acted as an affinity agent for nucleic acids. Less than 1 ng/L of cell-free DNA was detected evidenced by fluorescent DAPI molecules captured on the DNA held on the capture particles.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of detecting one or more different populations of target rare molecules in a sample suspected of containing the one or more different populations of rare molecules and non-rare molecules, the method comprising:
   (a) enhancing the concentration of the one or more different populations of target rare molecules over that of the non-rare molecules to form a concentrated sample,
   (b) incubating the concentrated sample with, for each different population of target rare molecules, an affinity agent that comprises a specific binding partner that is specific for and binds to a target rare molecule of one of the populations of the target rare molecules wherein the affinity agent comprises a mass spectrometry label precursor or a first alteration agent with a mass spectrometry label precursor and wherein the affinity agent may be non-particulate or particulate and wherein the first alteration agent either facilitates the formation of a mass spectrometry label from the mass spectrometry label precursor or releases an entity that comprises the mass spectrometry label precursor from the affinity agent,
   (c) forming a retentate and a filtrate by contacting the incubated sample with a porous matrix,
   (d) if the first alteration agent does not facilitate the formation of a mass spectrometry label from the mass spectrometry label precursor, then subjecting one or both of the retentate and the filtrate to a second alteration agent that facilitates the formation of a mass spectrometry label from the mass spectrometry label precursor from the affinity agent,
   (e) subjecting one or both of the retentate and the filtrate to mass spectrometry analysis to determine the presence and/or amount of each different mass spectrometry label, and
   (f) relating the presence and/or amount of each different mass spectrometry label to the present and/or amount of each different population of target rare molecules in the sample.

2. The method according to claim 1, wherein the specific binding partner of the affinity agent is selected from the group consisting of antibodies and nucleic acids.

3. The method according to claim 1, wherein at least one different population of the target rare molecules is associated with rare cells.

4. The method of claim 3, wherein the rare cells are human cells, bacterial cells or viral cells.

5. The method according to claim 1, wherein the affinity agent is particulate and comprises at least one carrier particle to which is linked at least one label particle wherein the label particle comprises a mass spectrometry label precursor.

6. The method according to claim 5, wherein the affinity reagent comprises more than one carrier particle wherein each of the carrier particles is linked to one another by a linking group.

7. The method according to claim 5 wherein the affinity agent, carrier particle, label particle and mass spectrometry label precursor are connected by at least one linking group.

8. The method according to claim 7 wherein the linking group is cleavable.

9. The method according to claim 5 wherein the carrier particle, label particle, linking group or mass spectrometry label precursor is fluorescent.

10. The method according to claim 5, wherein the carrier particle or the label particle is magnetic.

11. The method according to claim 5, wherein the label particle is magnetic and is removed from the membrane by punching out, filtration, extraction, or pickup.

12. The method according to claim 1, wherein step (c) comprises disposing the concentrated sample on a side of a porous matrix and applying vacuum to the disposed concentrated sample wherein the vacuum applied is about 1 millibar to about 100 millibar and wherein the pore size of the porous matrix is about 1 μm to about 100 μm.

13. A method of detecting one or more different populations of target rare cells in a sample suspected of containing the one or more different populations of rare cells and non-rare cells, the method comprising:
   (a) enhancing the concentration of the one or more different populations of target rare cells over that of the non-rare cells to form a concentrated sample,
   (b) incubating the concentrated sample with, for each different population of target rare cells, a mass spectrometry label precursor and an alteration agent that facilitates the formation of a mass spectrometry label from the mass spectrometry label precursor wherein the mass spectrometry label precursor or the alteration agent is part of an affinity agent that is specific for a target rare cell of one of the populations of the target rare cells,
   (c) disposing the concentrated sample on a side of a porous matrix and applying vacuum to the disposed concentrated sample to form a retentate and a filtrate,
   (d) subjecting one or both of the retentate and the filtrate to mass spectrometry analysis to determine the presence and/or amount of each different mass spectrometry label, and
   (e) relating the presence and/or amount of each different mass spectrometry label to the present and/or amount of each different population of target rare cells in the sample.

14. The method according to claim 13, wherein the affinity agent is selected from the group consisting of antibodies and nucleic acids.

15. The method according to claim 13, wherein the alteration agent acts to facilitate cleavage of the mass spectrometry label precursor to form the mass spectrometry label or wherein the alteration agent acts to facilitate reaction of the mass spectrometry label precursor with a moiety to form the mass spectrometry label.

16. A method of detecting one or more different populations of target rare molecules in a sample suspected of containing the one or more different populations of rare molecules and non-rare molecules, the method comprising:

(a) incubating (i) a sample that has an enhanced concentration of the one or more different populations of target rare molecules over that of the non-rare molecules wherein the target rare molecules are in particulate form, and (ii) for each different population of target rare molecules, an affinity agent that comprises a specific binding partner that is specific for and binds to a target rare molecule of one of the populations of the target rare molecules wherein the affinity agent comprises a mass spectrometry label precursor or a first alteration agent with a mass spectrometry label precursor and wherein, for each different population of target rare molecules, the affinity agent comprises a particle reagent and wherein the first alteration agent either facilitates the formation of a mass spectrometry label from the mass spectrometry label precursor or releases an entity that comprises the mass spectrometry label precursor from the affinity agent, and wherein, during the incubating, for each different population of target rare molecules, particle aggregates are formed from the particle reagent of the affinity agent, (b) forming a retentate and a filtrate by contacting the incubated sample with a porous matrix, (c) if the first alteration agent does not facilitate the formation of a mass spectrometry label from the mass spectrometry label precursor, then subjecting one or both of the retentate and the filtrate to a second alteration agent that facilitates the formation of a mass spectrometry label from the mass spectrometry label precursor from the affinity agent for each different population of target rare molecules, (d) subjecting one or both of the retentate and the filtrate to mass spectrometry analysis to determine the presence and/or amount of each different mass spectrometry label, and (e) relating the presence and/or amount of each different mass spectrometry label to the present and/or amount of each different population of target rare molecules in the sample.

17. The method according to claim 16 wherein prior to step (a), for each different population of target rare molecules not in particulate form, the method comprises:

(A) combining the sample with one or more particle entities wherein each particle entity comprises a binding partner for the target rare molecule for each of the populations of target rare molecules that is not in particulate form to form particle-bound target rare molecules, and (B) subjecting the sample to a filtration procedure to form a sample that has an enhanced concentration of the one or more different populations of target rare molecules over that of the non-rare molecules.

18. The method according to claim 17, wherein the particle entity, the carrier particle, or the label particle is magnetic.

19. The method according to claim 16, wherein the affinity agent is selected from the group consisting of antibodies and nucleic acids.

20. The method according to claim 16, wherein the alteration agent acts to facilitate cleavage of the mass spectrometry label precursor to form the mass spectrometry label or wherein the alteration agent acts to facilitate reaction of the mass spectrometry label precursor with a moiety to form the mass spectrometry label.

* * * * *

SEQUENCE LISTING

```
<160> NUMBER OF SEQ ID NOS: 9

<210> SEQ ID NO 1
<211> LENGTH: 20
<212> TYPE: PRT
<213> ORGANISM: Homo sapiens
<220> FEATURE:
<221> NAME/KEY: MISC_FEATURE
<222> LOCATION: (10)..(11)
<223> OTHER INFORMATION: Xaa means cysteine linked through the
      sulfhydryl bond

<400> SEQUENCE: 1

Ile Gly Met Thr Ser Arg Tyr Phe Cys Xaa Xaa Cys Phe Tyr Arg Ser
1               5                   10                  15

Thr Met Gly Ile
            20

<210> SEQ ID NO 2
<211> LENGTH: 9
<212> TYPE: PRT
<213> ORGANISM: Homo sapiens
```

```
<400> SEQUENCE: 2

Ile Gly Met Thr Ser Arg Tyr Phe Cys
1               5

<210> SEQ ID NO 3
<211> LENGTH: 9
<212> TYPE: PRT
<213> ORGANISM: Homo sapiens

<400> SEQUENCE: 3

Ile Gly Met Gly Ser Arg Tyr Phe Cys
1               5

<210> SEQ ID NO 4
<211> LENGTH: 9
<212> TYPE: PRT
<213> ORGANISM: Homo sapiens

<400> SEQUENCE: 4

Ile Gly Met Thr Ser Arg Tyr Phe Cys
1               5

<210> SEQ ID NO 5
<211> LENGTH: 27
<212> TYPE: PRT
<213> ORGANISM: Homo sapiens

<400> SEQUENCE: 5

Ile Leu Glu Gly Leu Tyr Met Glu Thr Thr His Arg Ser Glu Arg Ala
1               5                   10                  15

Arg Gly Thr Tyr Arg Pro His Glu Cys Tyr Ser
            20                  25

<210> SEQ ID NO 6
<211> LENGTH: 9
<212> TYPE: PRT
<213> ORGANISM: Homo sapiens

<400> SEQUENCE: 6

Ile Gly Met Thr Ser Arg Tyr Phe Cys
1               5

<210> SEQ ID NO 7
<211> LENGTH: 9
<212> TYPE: PRT
<213> ORGANISM: Homo sapiens

<400> SEQUENCE: 7

Ile Gly Met Thr Ser Arg Tyr Phe Cys
1               5

<210> SEQ ID NO 8
<211> LENGTH: 9
<212> TYPE: PRT
<213> ORGANISM: Homo sapiens

<400> SEQUENCE: 8

Ile Gly Met Thr Ser Arg Tyr Phe Cys
1               5

<210> SEQ ID NO 9
<211> LENGTH: 9
<212> TYPE: PRT
```

-continued

```
<213> ORGANISM: Homo sapiens

<400> SEQUENCE: 9

Ile Gly Met Thr Ser Arg Tyr Phe Cys
1               5
```